(12) United States Patent
Tavernier et al.

(10) Patent No.: US 11,246,911 B2
(45) Date of Patent: Feb. 15, 2022

(54) IMMUNE-CELL TARGETED BISPECIFIC CHIMERIC PROTEINS AND USES THEREOF

(71) Applicants: VIB VZW, Ghent (BE); Universiteit Gent, Ghent (BE); Centre National de la Recherche Scientifique, Paris (FR); Universite de Montpellier, Montpellier (FR)

(72) Inventors: Jan Tavernier, Ghent (BE); Jose Van Der Heyden, Ghent (BE); Genevieve Garcin, Ghent (BE); Gilles Uze, Ghent (BE); Yann Bordat, Ghent (BE)

(73) Assignees: VIB VZW, Ghent (BE); Centre National de la Recherche Scientifique, Paris (FR); Univeriteit Gent, Ghent (BE); Universite de Montpellier, Montpellier (FR)

(*) Notice: Subject to any disclaimer, the term of this patent is extended or adjusted under 35 U.S.C. 154(b) by 337 days.

(21) Appl. No.: 16/475,305

(22) PCT Filed: Feb. 6, 2018

(86) PCT No.: PCT/EP2018/052902
§ 371 (c)(1),
(2) Date: Jul. 1, 2019

(87) PCT Pub. No.: WO2018/146074
PCT Pub. Date: Aug. 16, 2018

(65) Prior Publication Data
US 2019/0351021 A1    Nov. 21, 2019

Related U.S. Application Data

(60) Provisional application No. 62/455,709, filed on Feb. 7, 2017.

(51) Int. Cl.
| | | |
|---|---|---|
| A61K 47/64 | (2017.01) | |
| A61K 47/68 | (2017.01) | |
| C07K 14/56 | (2006.01) | |
| C07K 14/725 | (2006.01) | |
| C07K 16/28 | (2006.01) | |
| A61K 38/21 | (2006.01) | |
| A61K 39/395 | (2006.01) | |
| A61K 38/20 | (2006.01) | |

(52) U.S. Cl.
CPC ............ A61K 38/20 (2013.01); A61K 47/642 (2017.08); A61K 47/6813 (2017.08); C07K 14/56 (2013.01); C07K 14/7051 (2013.01); C07K 16/2887 (2013.01); C07K 2317/24 (2013.01); C07K 2317/622 (2013.01); C07K 2319/73 (2013.01)

(58) Field of Classification Search
None
See application file for complete search history.

(56) References Cited

U.S. PATENT DOCUMENTS

| | | |
|---|---|---|
| 5,914,254 A | 6/1999 | Mascarenhas et al. |
| 8,541,564 B2 | 9/2013 | Lillard, Jr. |
| 8,796,422 B2 | 8/2014 | Lillard, Jr. |
| 8,980,267 B2 | 3/2015 | Grewal et al. |
| 8,987,210 B2 | 3/2015 | Lilliard, Jr. |
| 9,139,634 B2 | 9/2015 | Morrison et al. |
| 9,371,389 B2 | 6/2016 | Sakamoto et al. |
| 9,492,562 B2 | 11/2016 | Tavernier et al. |
| 9,534,056 B2 | 1/2017 | Grewal et al. |
| 9,732,135 B2 | 8/2017 | Tavernier et al. |
| 9,878,014 B2 | 1/2018 | Tavernier et al. |
| 10,034,919 B2 | 7/2018 | Tavernier et al. |
| 2002/0193569 A1 | 12/2002 | Hanna |
| 2007/0071675 A1* | 3/2007 | Wu .................... A61P 25/06 424/1.49 |
| 2010/0028341 A1 | 2/2010 | Hermans et al. |
| 2010/0172868 A1 | 7/2010 | Morrison et al. |
| 2010/0297076 A1 | 11/2010 | Morrison et al. |
| 2011/0020273 A1 | 1/2011 | Chang et al. |
| 2011/0081341 A1 | 4/2011 | Honjo et al. |
| 2011/0104112 A1 | 5/2011 | Morrison et al. |
| 2011/0224407 A1 | 9/2011 | Langer et al. |
| 2011/0274658 A1 | 11/2011 | Silver et al. |

(Continued)

FOREIGN PATENT DOCUMENTS

| | | |
|---|---|---|
| WO | WO 91/02754 | 3/1991 |
| WO | WO 03/033720 A2 | 4/2003 |

(Continued)

OTHER PUBLICATIONS

Rossi et al. Cancer Res., vol. 70(19), pp. 7600-7609 (Year: 2010).*

(Continued)

*Primary Examiner* — Gary B Nickol
*Assistant Examiner* — Jegatheesan Seharaseyon
(74) *Attorney, Agent, or Firm* — Morgan, Lewis & Bockius LLP

(57) ABSTRACT

The present invention relates, in part, to targeted chimeric proteins with beneficial therapeutic effects, including, for example, effects mediated by chimeric proteins which comprise modified signaling agents two or more targeting moieties. Methods of treatment and pharmaceutical compositions comprising the chimeric proteins are also provided. The present invention finds use in the treatment of various disease and disorders.

14 Claims, 19 Drawing Sheets
Specification includes a Sequence Listing.

(56) References Cited

U.S. PATENT DOCUMENTS

| | | |
|---|---|---|
| 2013/0183298 A1 | 7/2013 | Le et al. |
| 2013/0245236 A1 | 9/2013 | Kroczek |
| 2014/0348789 A1 | 11/2014 | Tavernier et al. |
| 2015/0139951 A1 | 5/2015 | Grewal et al. |
| 2016/0115214 A1 | 4/2016 | Lillard, Jr. |
| 2019/0010199 A1 | 1/2019 | Tavernier et al. |

FOREIGN PATENT DOCUMENTS

| | | | |
|---|---|---|---|
| WO | WO 2006/053883 A1 | 5/2006 | |
| WO | WO 2006/115800 A2 | 11/2006 | |
| WO | WO 2008/014612 A1 | 2/2008 | |
| WO | WO 2008/124086 A2 | 10/2008 | |
| WO | WO 2009/003145 A1 | 12/2008 | |
| WO | WO 2009/039409 A1 | 3/2009 | |
| WO | WO 2010/036918 A2 | 4/2010 | |
| WO | WO 2010/066740 A1 | 6/2010 | |
| WO | WO 2011/020783 A2 | 2/2011 | |
| WO | WO 2011020783 A2 | 2/2011 | |
| WO | WO 2011/029870 A1 | 3/2011 | |
| WO | WO 2012107416 A2 | 8/2012 | |
| WO | WO 2012/170072 A1 | 12/2012 | |
| WO | WO 2013/059885 A2 | 5/2013 | |
| WO | WO 2013/107791 A1 | 7/2013 | |
| WO | WO 2013/134138 A1 | 9/2013 | |
| WO | WO 2013134138 A1 | 9/2013 | |
| WO | WO 2014/164680 A1 | 10/2014 | |
| WO | WO 2015/007520 A1 | 1/2015 | |
| WO | WO 2015/007536 A2 | 1/2015 | |
| WO | WO 2015/007542 A1 | 1/2015 | |
| WO | WO 2015/007903 A1 | 1/2015 | |
| WO | WO 2017/007382 A1 | 5/2017 | |

OTHER PUBLICATIONS

Garcin, et al., "High efficiency cell-specific targeting of cytokine activity," Nature Communications, vol. 5, No. 8, Jan. 8, 2014, pp. 2-8.

International Search Report & Written Opinion, PCT Application No. PCT/EP2018/052902, dated Apr. 9, 2018, 17 pages.

Acres, B., et al., "Fusokine Interleukin-2/Interleukin-18, a Novel Potent Innate and Adaptive Immune Stimulator with Decreased Toxicity", Cancer Res., vol. 65, No. 20, pp. 9536-9546, 2005.

Baba, M., et al., "Identification of CCR6, the Specific Receptor for a Novel Lymphocyte-Directed CC Chemokine ARC", The Journal of Biological Chemistry vol. 272, No. 23, p. 14893-14898, 1997.

Barbara, J. A., et al., "Dissociation of TNF-alpha cytotoxic and proinflammatory activities by p55 receptor- and p75 receptor-selective TNF-alpha mutants," EMBO Journal, vol. 13, No. 4, pp. 843-850, 1994.

Bork, et al., "Go hunting in sequence databases but watch out for the traps," Trends in Genetics, vol. 12, pp. 425-427, 1996.

Bork, "Powers and Pitfalls in Sequence Analysis: The 70% Hurdle," Genome Research, 10:398-400, 2000.

Boschert, et al., "Single chain TNF derivatives with individually mutated receptor binding sites reveal differential stoichiometry of ligand receptor complex formation forTNFR1 and TNFR2," Cellular Signalling 22 (7):1088-1096, 2010.

Bremer, et al., "Superior activity of fusion protein scFvRit:sFasL over cotreatment with rituximab and Fas agonists," Cancer Res., 68:597-604, 2008.

Camacho, N.P., et al., "Structure of an Interleukin-1β Mutant With Reduced Bioactivity Shows Multiple Subtle Changes in Conformation That Affect Protein-Protein Recognition", Biochemistry, vol. 32, No. 34, pp. 8749-8757, 1993.

Coulstock, et al., "Liver-targeting of Interferon-alpha with Tissue-Specific Domain Antibodies," Plos One, vol. 8, No. 2., pp. 1-11, Feb. 2013.

De Bruyn, M., et al., "Antibody-Based Fusion Proteins to Target Death Receptors in Cancer", Cancer Letters, vol. 332, pp. 175-183, 2013.

Deffar, et al., "Nanobodies—The New Concept in Antibody Engineering," African Journal of Biotechnology, vol. 8 No. 12, pp. 2645-2652, 2009.

Dijkmans, R., et al., "Murine Interferon-T/Interleukin-1 Fusion Proteins Used as Antigens for the Generation of Hybridomas Producing Monoclonal Anti-Interleukin-1 Antibodies", Cytokine, vol. 3, No. 2, pp. 134-140, 1991.

Dimitrov, D. S., "Engineered CH2 Domains (Nanoantibodies)", mAbs, Landes Bioscience, vol. 1, No. 1, pp. 6-28, 2009.

Frey, K., et al., "Antibody-Based Targeting of Interferon-Alpha to the Tumor Neovasculature: A Critical Evaluation", Integrative Biology, vol. 3, pp. 468-478, 2009.

Garcin, G., et al., "High Efficiency Cell-Specific Targeting of Cytokine Activity", Nature Communications, pp. 1-9, 2014.

Garlanda, et al., "The Interleukin-1 Family: Back to the Future", Immunity, 39(6) 1003-1018, Dec. 12, 2013.

Holler, N., et al, "Two Adjacent Trimeric Fas Ligands are Required for Fas Signaling and Formation of a Death-Inducing Signaling Complex", Molecular and Cellular Biology, vol. 23, No. 4, pp. 1428-1440, 2003.

Huang, T., et al., "A Trimeric Anti-HER2/neu ScFv and Tumor Necrosis Factor-α Fusion Protein Induces HER2/neu Signaling and Facilitates Repair of Injured Epithelia", The Journal of Pharmacology and Experimental Therapeutics, vol. 316, No. 3, pp. 983-991, 2008.

International Search Report, PCT/EP2013/050787, dated Jun. 14, 2013, 9 pages.

International Search Report, PCT/EP2017/055312, dated Sep. 14, 2017, 6 pages.

Krippner-Heidenreich, A., et al., "Single-Chain TNF, a TNF Derivative with Enhanced Stability and Antitumoral Activity", The Journal of Immunology, vol. 180, pp. 8176-8183, 2008.

Loetscher, H., et al., "Human Tumor Necrosis Factor alpha (TNFalpha) Mutants with Exclusive Specificity for the 55-kDa or 75-kDa TNF Receptors," Journal of Biological Chemistry, American Society for Biochemistry and Molecular Biology, US, vol. 268, No. 35, pp. 26350-26357, 1993.

Masci, et al., "New and Modified Interferon alfas: Preclinical and Clinical Data," Current Oncology Reports, vol. 5, No. 2, Mar. 1, 2003.

Ngo, et al., "Computational Complexity, Protein Structure Prediction, and the Levinthal Paradox," The Protein Folding Problem and Tertiary Structure Prediciton, pp. 492-495, 1994.

Pan, M., et al., "Mutation of the IFNAR-1 Receptor Binding Site of Human IFN-α2 Generates Type I IFN Competitive Antagonists", Biochemistry, vol. 47, pp. 12018-12027, 2008.

Patris, et al., "Nanoimmunoassay onto a screen printed electrode for HER2 breast cancer biomarker determination", Taianta, vol. 130, pp. 164-170, 2014.

Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, pp. 9020-9028, 2009.

Piehler, et al., "New Structural and Functional Aspects of the Type I Interferon-Receptor Interaction Revealed by Comprehensive Mutational Analysis of the Binding Interface," The Journal of Biological Chemistry, vol. 275, No. 51, pp. 40425-40433, Dec. 22, 2000.

Rafei, M., et al., "An Engineered GM-CSF-CCL2 Fusokine is a Potent Inhibitor of CCR2-Driven Inflammation as Demonstrated in a Murine Model of Inflammatory Arthritis", The Journal of Immunology, vol. 183, pp. 1759-1766, 2009.

Rafei, M., et al., "A MCP1 Fusokine with CCR2-Specific Tumoricidal Activity", Molecular Cancer, vol. 10, No. 121, pp. 1-11, 2011.

Roisman, et al., "Structure of the interferon-receptor complex determined by distance constraints from doublemutant cycles and flexible docking," Proceedings of the National Academy of Sciences, vol. 98, No. 23, pp. 13231-13236, Nov. 6, 2001.

Rovero, S., et al., "Insertion of the DNA for the 163-171 Peptide of IL 1β Enables a DNA Vaccine Encoding p185$^{neu}$ to Inhibit Mammary Carcinogenesis in Her-2/neu Transgenic BALB/c Mice", Gene Therapy, vol. 8, pp. 147-452, 2001.

(56) References Cited

OTHER PUBLICATIONS

Schutyser, E., et al., "The CC Chemokine CCL20 and its Receptor CCR6", Cytokine & Growth Factor Reviews, vol. 14, pp. 409-426, 2003.

Vaneycken, et al., "Preclinical Screening of Anti-HER2 Nanobodies for Molecular Imaging of Breast Cancer", The FASEB Journal, vol. 25, pp. 2433-2446, 2011.

Weber, H., et al., "Single Amino Acid Changes that Render Human IFN-α2 Biologically Active on Mouse Cells", The EMBO Journal, vol. 6, No. 3, pp. 591-598, 1987.

Wells, "Additivity of Mutational Effects in Proteins," Biochemistry, vol. 29, No. 37, pp. 8509-8517, Sep. 18, 1990.

Wesolowski, et al., "Single Domain Antibodies: Promising Experimental and Therapeutic Tools in Infection and Immunity", Med Microbiol Immunol., vol. 198, pp. 157-174, 2009.

\* cited by examiner

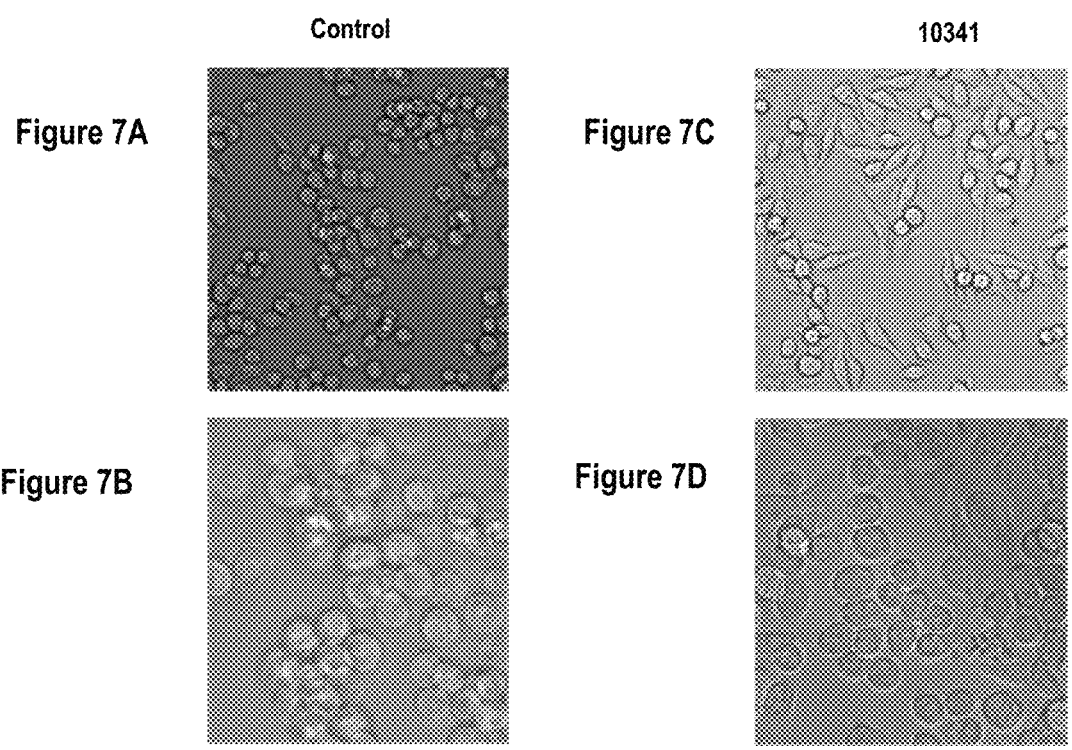

IMMUNE-CELL TARGETED BISPECIFIC CHIMERIC PROTEINS AND USES THEREOF

CROSS-REFERENCE TO RELATED APPLICATIONS

This application is a 371 national entry of PCT/EP2018/052902, filed Feb. 6, 2018 and claims the benefit of and priority to U.S. Provisional Patent Application No. 62/455,709, filed Feb. 7, 2017, the entire contents of which are hereby incorporated by reference in their entireties.

FIELD

The present invention relates, in part, to targeted chimeric proteins that can recruit effector cells and deliver signaling to provide beneficial therapeutic effects. The present invention also provides pharmaceutical compositions comprising the chimeric proteins as well as their use in the treatment of various diseases and disorders.

SEQUENCE LISTING

The instant application contains a Sequence Listing which has been submitted in ASCII format via EFS-Web and is hereby incorporated by reference in its entirety. Said ASCII copy, created on Feb. 1, 2017, is named ORN-023PC_ST245.txt and is 16,384 bytes in size.

BACKGROUND

Agents such as cytokines, hormones, and growth factors are naturally occurring substances capable of modulating cellular growth and differentiation. These signaling agents play important roles in a variety of physiological processes including, for example, metabolism, respiration, sleep, excretion, healing, movement, reproduction, mood, stress, tissue function, immune function, sensory perception, and growth and development. Typically, cytokines, hormones, and growth factors exert their biological effects through binding to specific receptors on the surface of target cells.

Type I interferons are cytokines involved in anti-tumor immune responses and in promoting the survival and proliferation of T-cells, B-cells, natural killer (NK) cells as well as the activation of dendritic cells. Type I interferons also elevate the expression of tumor antigens on neoplastic cells thereby increasing their immunogenicity. As such, Type I interferons may be utilized in anti-cancer treatments (Escobar et al., 2014). Type I interferons bind to a heterodimeric cell surface receptor, the Interferon-$\alpha/\beta$ receptor (IFNAR), which is comprised of the IFNAR1 and IFNAR2 subunits. Binding of the type I interferons to the IFNAR activates the JAK-STAT signalling pathway to elicit various biological effects (Weerd et al., 2007).

Chemokines (chemoattractant cytokines) are a family of about fifty secreted proteins implicated in the regulation of cell motility, a cellular behaviour important for many biological processes ranging from development to immune and inflammatory responses. Chemokine family members show a high level of conservation in their tertiary structures which include three anti-parallel $\beta$-sheets and a single $\alpha$-helix. The bioactivities of chemokines are initiated by binding to cellular receptors. Chemokine receptors include a family of G protein-coupled receptors (GPCRs) having seven transmembrane domains, and their expressions are usually tissue-specific. There are about twenty receptors for the fifty characterized chemokines. By way of example, XCL1 (also known as lymphotactin) is a chemokine produced by T, NK and natural killer T (NKT) cells. Its only known receptor is XCR1 which is specifically expressed at the surface of dendritic cell subtypes that are capable of antigen cross-presentation. Binding of XCL1 to XCR1 is important in the expansion and differentiation of cytotoxic T cells (Dorner et al. 2009).

Targeting of cell surface antigens may also modulate cellular growth and differentiation. Cell surface antigens are markers for different cell types and are selectively expressed on the surface of different pathological cells. Cell surface antigens may be targeted by antibodies which specifically recognize these antigens. CD20 is a B-lymphocyte antigen that is expressed on the surface of B cells, and plays a critical role in B-cell development, differentiation, and cell-cycle initiation events. Further, CD20 is not only a B-cell differentiation marker but is also considered a tumor marker. High levels of CD20 are detected in patients with B-cell lymphomas and leukemias. CD20 remains on the surface of B cells and does not internalize upon binding with an anti-CD20 antibody, nor circulates as a soluble free antigen (MD Pescovitz 2006). These characteristics make CD20 a good candidate for therapeutic antibody targeting. For example, antibodies directed against CD20 are used to treat B cell non-Hodgkin lymphoma (Carter et al. 2009).

Clinically, cytokines, hormones, and growth factors are used in the treatment of a variety of diseases and disorders including, for example, cancers, microbial infections, hematological disorders, and metabolic diseases. Despite this common use, the administration of these signaling agents is not without risks. Particularly, the therapeutic use of cytokines, hormones, and growth factors is often associated with systemic toxicity and deleterious side effects thus limiting the dose levels that these agents can be used. As a result, only relatively small numbers of cytokines are currently approved by regulatory agencies. Of these, fourteen of the FDA-approved cytokine preparations carry warnings, ten of which are black box warnings. Furthermore, and relatedly, many of these signaling agents have promiscuous binding activity and therefore provide for the possibility of off-target effects, which can underlie deleterious side effects or, at the least, provide a sink for the therapeutic construct away from the site of therapeutic action.

There remains a need to develop therapeutic agents with improved safety and efficacy.

SUMMARY OF THE INVENTION

Accordingly, in various aspects, the present invention provides a chimeric protein having two or more targeting moieties comprising recognition domains which specifically bind to antigens or receptors of interest, wherein the antigens or receptors of interest include CD20 and XCR1. In some embodiments, the chimeric protein comprises a targeting moiety comprising the chemokine XCL1 or a functional equivalent thereof. In such embodiments, the chemokine XCL1 or a functional equivalent thereof binds to the chemokine receptor XCR1. In some embodiments, the chimeric protein further comprises a targeting moiety comprising a recognition domain that binds CD20. In such embodiments, the targeting moiety may be anti-CD20 antibody, or a derivative thereof. For example, the anti-CD20 antibody may be a monoclonal antibody selected from Rituximab, Rbinutuzumab, Ofatumumab, Ibritumomab tiuxetan, Ocaratuzumab, Ocrelizumab, TRU-015, Veltuzumab, Tositumomab, or a derivative thereof. In another exemplary embodiment, the targeting moiety is a camelid heavy chain antibody ($V_{HH}$) that specifically binds to CD20.

In various embodiments, the chimeric protein further comprises a modified signaling agent. In some embodiments, the modified signaling agent is a variant type I interferon. In some embodiments, the variant type I interferon has reduced affinity and/or activity at a cell signaling receptor, which is optionally a multi-subunit signaling receptor. In various embodiments, the modified signaling agent has one or more mutations that confer improved safety as compared to a wild type signaling agent. In some embodiments, the modified signaling agent has a one or more point mutations to reduce its binding affinity and/or activity at a cell signaling receptor such as IFNAR. In an exemplary embodiment, the modified signaling agent present in the chimeric protein is IFN-α. In such an embodiment, methods of the invention may be used to exert a localized effect of IFN-α.

In various embodiments, the chimeric protein having two or more targeting moieties and a modified signaling agent are optionally connected with a linker. In various embodiments, the two or more targeting moieties are optionally connected with a linker. In these embodiments, the linkers connect the N-terminus and/or the C-terminus of the two or more targeting moieties. In some embodiments, the linker connects the N-terminus and/or the C-terminus of the modified signaling agent to the two or more targeting moieties. In some embodiments, the linker connects the modified signaling agent and targeting moieties in an orientation in which the modified signaling agent is adjacent to at least two targeting moieties. In various embodiments, the linkers connect the modified signaling agent and targeting moieties in an orientation in which the modified signaling agent is adjacent to one targeting moiety and the targeting moiety which specifically binds to CD20 is at the N-terminus or C-terminus. In some embodiments, the linkers connect the modified signaling agent and targeting moieties in an orientation in which the modified signaling agent is adjacent to one targeting moiety and the targeting moiety which specifically binds to XCR1 is at the N-terminus or C-terminus.

In various embodiments, the present invention further relates to a pharmaceutical formulation comprising the chimeric protein of the invention and a pharmaceutically acceptable carrier. In some embodiments, the present invention relates to a recombinant nucleic acid composition encoding one or more of the chimeric proteins of the present invention. In some embodiments, the present invention relates to a host cell comprising the recombinant nucleic acid.

In various embodiments, the chimeric protein of the invention is targeted to B-cells, wherein the chimeric protein induces B-cells adherence. In various embodiments, the chimeric proteins of the present invention induce a decrease in B-cells circulation in vivo.

In various embodiments, the present chimeric protein finds use in the treatment of various disease or disorders including cancer, infections, immune disorders, autoimmune diseases, cardiovascular diseases, wound, ischemia-related diseases, neurodegenerative diseases, and/or metabolic diseases.

BRIEF DESCRIPTION OF THE FIGURES

FIGS. 7A-D. Compound 10341 induced adherence of A20 B cells. A20 cells were cultured on 24-well plate (FIGS. 7A and 7C) or on CELLview Glass Bottom Dish, TC-treated (FIGS. 7B and 7D) and treated with compound 10341 (2 µg/ml) for 4 hours (FIGS. 7B and 7D) to 18 hours (FIGS. 7A and 7C) at 37° C. Cells treated with PBS served as negative controls. Cells were then observed under either a Spinning Disk microscope (×20 optical plus ×1.5 numerical zoom) (panel A) or the Axiovert 200M Zeiss inverted microscope (×40).

FIG. 8A: Balb/c splenocytes were incubated first with a 100-fold molar excess of either mouse CD20 VHH (compound 9075) or compound 10121 (mCD20nb-IFNα2R149A) for 15 minutes at 37° C. Compound 10058 (2 µg/ml) was subsequently added for a further 30 minutes incubation time. Cells were then scraped, labelled with anti-CD19 antibody and analyzed by FACS. FIG. 8B: Same experiment as in FIG. 8A except that cells were pre-incubated with 10 µg of rat anti-mouse CD20 antibody (eBioscience 14-0201-82). FIG. 8C: Balb/c splenocytes were treated with compound 10058 (2 µg/ml), compound 10058 plus a 50-fold molar excess of compound 9737, compound 9737 plus compound 9735 (same molarity as compared to compound 10058 for each). Cells treated with PBS served as negative controls. Cells were recovered and analyzed as described in FIG. 8A.

FIG. 12A: Compound 10341 (20 µg) was injected intravenously into Balb/c mice and sample of peripheral blood were collected 10 minutes or 4 hours later. Cells were labelled with CD19 antibody and analyzed by FACS analysis. FIG. 12B: Compound 10341 (20 µg) was injected intravenously into C57Bl6 mice. Sample of peripheral blood were collected after 10 minutes (1). Twenty four hours later, the same mice were re-injected with compound 10341. Peripheral blood was collected after 10 minutes (2). Cells were labelled with CD19 antibody and analyzed by FACS analysis.

DETAILED DESCRIPTION

Figure 1A:
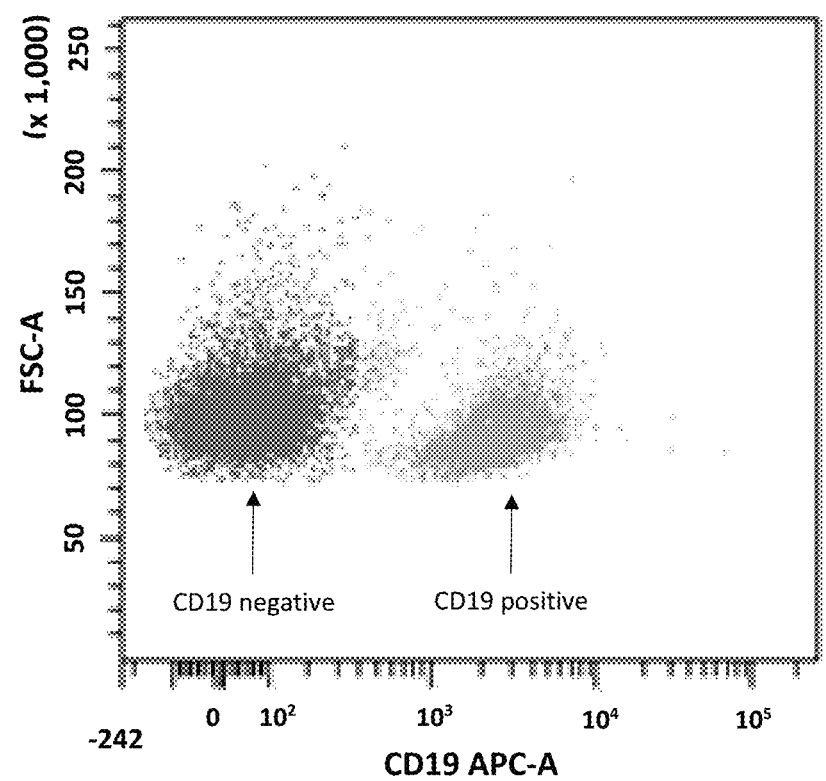
FIGS. 1A-B. IFN activity induced by compounds 10056 and 10058. FACS analysis of Balb/c splenocytes untreated (control) or treated with mCD20nb-300PAS-mXCL1/5xggs-IFNα2Q124R-his (2 µg/ml), mCD20nb-5xggs/mXCL1/ 5xggs-IFNα2Q124R-300PAS-his (2 µg/ml) or MuIFNα/β (10000 U/ml). CD19 positive and negative cell populations were identified by APC-labelled anti-CD19 antibody (FIG. 1A). CD11c high/CD8α positive cells as well as CD11c high/CD8α negative cells were identified by APC-labelled anti CD8α antibody and Alexa488-labelled anti CD11c antibody (FIG. 1B).

The present invention is based, in part, on the discovery of targeted bispecific chimeric proteins having targeting moieties that specifically recognize and bind CD20 and XCR1. In some embodiments, the bispecific chimeric proteins further include a modified signaling agent (e.g., IFN-α) with reduced affinity for one or more receptors. In various embodiments, the bispecific chimeric protein of the invention exhibit beneficial therapeutic properties and reduced side effects.

The present invention further provides pharmaceutical compositions comprising the chimeric proteins and their use in the treatment of various diseases. In various embodiments, administration of the chimeric proteins and/or pharmaceutical compositions of the invention achieve significantly reduced side effects compared to administration of the wild type signaling agent.

Chimeric Proteins

In various embodiments, the present invention relates to bi-specific or multi-specific chimeric proteins having two or more targeting moieties having recognition domains that specifically bind to a target (e.g. antigen, receptor) of interest. In some embodiments, the targeting moieties directly or indirectly recruit cells of relevance and/or modulate the function of the recruited cells. In some embodiments, the chimeric protein further comprises a signaling agent, which bears one or more mutations that render the signaling agent suitable for pharmaceutical use with minimal side effects (e.g. minimal cytokine storm-like effects, flu-like symptoms, suicidal thoughts, off-target side effects, among others).

In an exemplary embodiment, the present invention relates to bispecific chimeric proteins that comprise two or more targeting moieties, wherein one of the targeting moieties binds to the surface antigen CD20 and the other targeting moiety binds to the chemokine receptor XCR1. In an embodiment, the targeting moiety that binds to the CD20 is an anti-CD20 antibody. In another embodiment, the targeting moiety that binds XCR1 is the chemokine XCL1. In some embodiments, the bispecific chimeric protein further comprises a modified signaling agent such as a variant type I interferon, e.g. human IFN-α.

In various embodiments, the present chimeric proteins have two or more targeting moieties and optionally the modified signaling agent connected together via different configurations. In various embodiments, the two or more targeting moieties are optionally connected with a linker. In these embodiments, the linkers connect the N-terminus and/or the C-terminus of the two or more targeting moieties.

In various embodiments, the modified signaling agent and the two or more targeting moieties are optionally connected with a linker. In some embodiments, the linker connects the N-terminus and/or the C-terminus of the modified signaling agent to the two or more targeting moieties. In an embodiment, one of the targeting moieties is linked to the amino-terminus of the signaling agent and the other targeting moiety is linked to the carboxy-terminus of the signaling agent.

In various embodiments, the linker connects the modified signaling agent and targeting moieties in an orientation in which the modified signaling agent is adjacent to at least two targeting moieties. In one embodiment, the linkers connect the modified signaling agent and targeting moieties in an orientation in which the modified signaling agent is adjacent to one targeting moiety and the targeting moiety which specifically binds to CD20 is at the N-terminus or C-terminus. In one embodiment, the linkers connect the modified signaling agent and targeting moieties in an orientation in which the modified signaling agent is adjacent to one targeting moiety and the targeting moiety which specifically binds to XCR1 is at the N-terminus or C-terminus.

In another embodiment, both targeting moieties are linked to the amino-terminus of the signaling agent. For example, the amino-terminus of the signaling agent may be linked to the carboxy-terminus of one of the targeting moieties, which in turn is linked to the other targeting moiety (e.g., via its amino-terminus). In a further embodiment, both targeting moieties are linked to the carboxy-terminus of the signaling agent. For example, the carboxy-terminus of the signaling agent may be linked to the amino-terminus of one of the targeting moieties, which in turn is linked to the other targeting moiety (e.g., via its carboxy-terminus).

In various embodiments, the present chimeric proteins are in the form of a fusion protein having the components described herein.

In various embodiments, the present bispecific chimeric protein provides at least two therapeutic benefits when used pharmaceutically. For instance, the present chimeric protein may 1) effectively recruit immune effector cells to a site of required therapy, e.g. the tumor microenvironment, and 2) deliver one or more signals to the cells—e.g. immune effector cells and/or tumor cells—to promote a cancer reducing effect (e.g. provide immune cell stimulation from the modified signaling agent (IFN-α), provide immune co-stimulatory signals via the targeting moieties (XCL1 and/or anti-CD20 antibody), provide reduction or silencing of immune co-inhibitory signals via the targeting moieties (XCL1 and/or anti-CD20 antibody), etc.). Accordingly, as described herein, the present bispecific chimeric protein provides a platform of therapeutically-relevant options for the effective treatment of diseases via the immune system.

In some embodiments, the bispecific chimeric protein of the invention is targeted to B cells where it induces the adherence of B cells. In various embodiments, the adherence of B cells may induce or enhance immune responses, and/or result in a decrease in B cell circulation. Without wishing to be bound by theory, it is believed that treatments with the chimeric proteins of the invention induce cell adherence which will result in activation of the immune response and/or efficient immunotherapies.

As described herein, the present chimeric protein may have improved safety due to one or more modifications, e.g. mutations. In various embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In some embodiments, the present chimeric protein allows for efficient binding of the targeting moieties and the signaling agent to their antigens and receptors. For instance, in some embodiments, the chimeric protein allows for efficient binding of one of the targeting moieties, e.g. XCL1 or anti-CD20 antibody, and the signaling agent to receptors on the same cell (e.g., different receptors or antigens) as well as the efficient binding of the other targeting moiety, e.g. XCL1 or anti-CD20 antibody, to another cell.

As described elsewhere herein, in various embodiments, the signaling agent is mutated to provide attenuated activity, and the binding of the targeting moieties and the signaling agent to receptors on the same cell is sequential, e.g. targeting moiety/receptor binding preceding signaling agent/receptor binding or targeting moiety/antigen binding preceding signaling agent/receptor binding. For instance, in some embodiments the signaling agent by itself is significantly less active in its mutated form (e.g. relative to wild type) because it cannot efficiently bind to its receptor(s). Accordingly, chimeric proteins of the invention are useful to avoid unwanted side effects caused by the signaling agent binding to its natural receptor on non-target cells. However, the signaling agent is active on target cells because the targeting moiety(ies) compensates for the missing/insufficient binding (e.g., without limitation and/or avidity) required for substantial activation. In various embodiments, the chimeric proteins of the present invention have a modified (e.g. mutant) signaling agent which causes the signaling agent to be inactive en route to the site of therapeutic activity (e.g. in contact with a target cell, including a tumor cell) through the body and to have its effect substantially on specifically targeted cell types which greatly reduces undesired side effects In various embodiments, the present chimeric proteins have selective bioactivity, e.g. therapeutically-relevant bioactivity, towards targeted cells (e.g. tumor cells), but not towards cells that are not targeted (e.g. normal, non-tumor cells).

In various embodiments, the present chimeric proteins provide synergistic activity and/or therapeutic effects. In such embodiments, the activity and/or therapeutic effects of the chimeric proteins have improved therapeutic effects, e.g. synergistically greater, than the therapeutic effects of the individual components (i.e., the two or more targeting moieties and the signaling agent) administered alone or in combination via co-administration.

Targeting Moieties

In various embodiments, the present invention relates to bi-specific or multi-specific chimeric proteins having two or more targeting moieties having recognition domains that specifically bind to a target (e.g. antigen, receptor) of interest. In some embodiments, the present chimeric protein comprises targeting moieties in various combinations. In an illustrative embodiment, the present chimeric protein may comprise two or more targeting moieties, wherein at least one of the targeting moieties is antibody or derivative thereof. In another illustrative embodiment, the present chimeric protein may comprise two or more targeting moieties, wherein at least one targeting moiety is a natural ligand for cell receptors.

In some embodiments, the present invention relates to a chimeric protein comprising two or more targeting moieties, the targeting moieties comprising recognition domains which specifically bind to antigens or receptors of interest, wherein the antigens or receptors include CD20 and XCR1. For example, in some embodiments, the present chimeric protein comprises at least one targeting moiety having an antigen recognition domain that specifically binds to a target (e.g. antigen, receptor) associated with B cells. In some embodiments, the targeting moiety directly or indirectly recruits B cells, e.g., in some embodiments, to a therapeutic site (e.g. a locus with one or more disease cell or cell to be modulated for a therapeutic effect).

In an exemplary embodiment, the present chimeric protein comprises a targeting moiety having a recognition domain that recognizes the B-cell antigen CD20. In an embodiment, the recognition domain recognizes one or more linear epitopes present on CD20. As used herein, a linear epitope refers to any continuous sequence of amino acids present on CD20. In another embodiment, the recognition domain recognizes one or more conformational epitopes present on CD20. As used herein, a conformation epitope refers to one or more sections of amino acids (which may be discontinuous) which form a three-dimensional surface with features and/or shapes and/or tertiary structures capable of being recognized by an antigen recognition domain.

In some embodiments, the chimeric protein of the present invention may bind to the full-length and/or mature forms and/or isoforms and/or splice variants and/or fragments and/or any other naturally occurring or synthetic analogs, variants, or mutants of human CD20. In various embodiments, the present chimeric protein comprises a targeting moiety capable of specific binding to human CD20 without neutralization of CD20.

In some embodiments, the human CD20 comprises the amino acid sequence of

```
CD20 (SEQ ID NO: 1):
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP
```

In some embodiments, the present chimeric protein has one or more targeting moieties which selectively bind a CD20 polypeptide (e.g., a polypeptide having the amino acid sequence of SEQ ID NO:1).

In some embodiments, the present chimeric protein comprises at least one targeting moiety having a recognition domain that specifically binds to a target (e.g. antigen, receptor) associated with dendritic cells. In some embodiments, the targeting moiety directly or indirectly recruits dendritic cells, e.g., in some embodiments, to a therapeutic site (e.g. a locus with one or more disease cell or cell to be modulated for a therapeutic effect).

In an exemplary embodiment, the present chimeric protein comprises a targeting moiety having a recognition domain that recognizes an epitope present on XCR1. In an embodiment, recognition domain recognizes one or more linear epitopes present on XCR1. As used herein, a linear epitope refers to any continuous sequence of amino acids present on XCR1. In another embodiment, the recognition domain recognizes one or more conformational epitopes present on XCR1.

In some embodiments, the chimeric protein of the present invention may bind to the full-length and/or mature forms and/or isoforms and/or splice variants and/or fragments and/or any other naturally occurring or synthetic analogs, variants, or mutants of human XCR1. In various embodiments, the present chimeric protein comprises a targeting moiety capable of specific binding to human XCR1 without neutralization of XCR1.

In some embodiments, the human XCR1 comprises the amino acid sequence of

```
XCR1 (SEQ ID NO: 2):
MESSGNPESTTFFYYDLQSQPCENQAWVFATLATTVLYCLVFLLSLVGNS

LVLWVLVKYESLESLTNIFILNLCLSDLVFACLLPVWISPYHWGWVLGDF

LCKLLNMIFSISLYSSIFFLTIMTIHRYLSVVSPLSTLRVPTLRCRVLVT

MAVWVASILSSILDTIFHKVLSSGCDYSELTWYLTSVYQHNLFFLLSLGI

ILFCYVEILRTLFRSRSKRRHRTVKLIFAIWAYFLSWGPYNFTLFLQTLF

RTQIIRSCEAKQQLEYALLICRNLAFSHCCFNPVLYVFVGVKFRTHLKHV

LRQFWFCRLQAPSPASIPHSPGAFAYEGASFY
```

In some embodiments, the present chimeric protein has one or more targeting moieties which selectively bind a XCR1 polypeptide (e.g., a polypeptide having the amino acid sequence of SEQ ID NO:2).

In various embodiments, the targeting moieties of the present invention may be any protein-based agent capable of specific binding, such as an antibody or derivatives thereof. In an embodiment, the targeting moiety comprises an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the targeting moiety comprises antibody derivatives or formats. In some embodiments, the targeting moiety of the present chimeric protein is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterases; a plastic antibodies; a phylomer; a stradobodies; a maxibodies; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a F(ab')$_2$, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In an embodiment, the targeting moiety comprises a VHH. In some embodiments, the VHH is a humanized VHH or camelized VHH.

In some embodiments, the VHH comprises a fully human $V_H$ domain, e.g. a HUMABODY (Crescendo Biologics, Cambridge, UK). In some embodiments, fully human $V_H$ domain, e.g. a HUMABODY is monovalent, bivalent, or trivalent. In some embodiments, the fully human $V_H$ domain, e.g. a HUMABODY is mono- or multi-specific such as monospecific, bispecific, or trispecific. Illustrative fully human $V_H$ domains, e.g. a HUMABODIES are described in, for example, WO 2016/113555 and WO2016/113557, the entire disclosure of which is incorporated by reference.

In one embodiment, the targeting moiety comprises a single-domain antibody, such as VHH from, for example, an organism that produces VHH antibody such as a camelid, a shark, or a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3). VHHs are commercially available under the trademark of NANOBODIES.

For example, in some embodiments, the chimeric protein of the invention comprises one or more antibodies, antibody derivatives or formats, peptides or polypeptides, nanobodies or fusion proteins that selectively bind CD20. In some embodiments, the chimeric protein comprises a targeting moiety which specifically binds to CD20 is an anti-CD20 antibody or derivative thereof. In some embodiments, the chimeric protein comprises a targeting moiety which is a camelid heavy chain antibody (VHH) that specifically binds to CD20.

Targeting moieties that recognize and bind to CD20 are known in the art. In illustrative embodiments, the targeting moiety comprises an anti-CD20 antibody selected from Rituximab, Rbinutuzumab, Ofatumumab, Ibritumomab tiuxetan, Ocaratuzumab, Ocrelizumab, TRU-015, Veltuzumab, Tositumomab, or a derivative thereof.

In various embodiments, the targeting moieties may comprise a sequence that targets CD20 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any targeting moiety sequence which is known to recognize and bind to CD20 (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to targeting moiety sequence which is known to recognize and bind to CD20). In various embodiments, the targeting moieties of the invention may comprise any combination of heavy chain, light chain, heavy chain variable region, light chain variable region, complementarity determining region (CDR), and framework region sequences that is known to recognize and bind to CD20.

In another example, in some embodiments, the present chimeric protein comprises a targeting moiety which is a cytokine, ligand, or a hormone (e.g., a chemokine) that selectively binds to XCR1. In some embodiments, the targeting moiety is a natural ligand such as a chemokine. In an exemplary embodiment, the targeting moiety is the chemokine XCL1 or a functional equivalent thereof.

In some embodiments, the human chemokine XCL1 (Lymphotactin) has the amino acid sequence of:

XCL1 (SEQ ID NO: 3):
MRLLILALLGICSLTAYIVEGVGSEVSDKRTCVSLTTQRLPVSRIKTYTI

TEGSLRAVIFITKRGLKVCADPQATWVRDVVRSMDRKSNTRNNMIQTKPT

GTQQSTNTAVTLTG

In another illustrative embodiment, the targeting moiety is XCL2, which is another chemokine that recognizes and binds to XCR1.

In various embodiments, the targeting moieties of the present invention may comprise a sequence of the chemokine XCL1 that targets the chemokine receptor XCR1 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to SEQ ID NO:3 (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to SEQ ID NO:3).

In alternative embodiments, the targeting moiety against XCR1 may comprise any antibodies, antibody derivatives or formats, peptides or polypeptides, nanobodies or fusion proteins that selectively bind XCR1.

In various embodiments, the present chimeric proteins comprise a targeting moiety comprising an amino acid sequence having one or more amino acid mutations with respect to any targeting moiety sequence which is known to recognize and bind to CD20 and/or XCR1, including those disclosed herein. In various embodiments, the present chimeric protein comprises a targeting moiety comprising an amino acid sequence having one, or two, or three, or four, or five, or six, or seen, or eight, or nine, or ten, or fifteen, or twenty amino acid mutations with respect to any targeting moiety sequence which is known to recognize and bind to CD20 and/or XCR1, including those disclosed herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, lie; (2) neutral hydrophilic: Cys, Ser, Thr; Asn, Gin; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the present chimeric protein's capability to specifically bind to CD20 or XCR1. In various embodiments, the mutations do not substantially reduce the present chimeric protein's capability to specifically bind to CD20 or XCR1 without neutralizing CD20 or XCR1.

In various embodiments, the binding affinity of the present chimeric protein of the invention for the full-length and/or mature forms and/or isoforms and/or splice variants and/or fragments and/or monomeric and/or dimeric forms and/or any other naturally occurring or synthetic analogs, variants, or mutants (including monomeric and/or dimeric forms) of CD20 or XCR1 may be described by the equilibrium dissociation constant ($K_D$). In various embodiments, the present chimeric protein comprises a targeting moiety that binds to the full-length and/or mature forms and/or isoforms and/or splice variants and/or fragments and/or any other naturally occurring or synthetic analogs, variants, or mutants (including monomeric and/or dimeric forms) of CD20 or XCR1 with a $K_D$ of less than about 1 uM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 1 nM.

In various embodiments, the present chimeric protein comprises a targeting moiety that binds but does not functionally modulate the antigen of interest, i.e., CD20 or XCR1. For instance, in various embodiments, the targeting moiety of the present chimeric protein simply targets the antigen or receptor of interest but does not substantially functionally modulate (e.g. substantially inhibit, reduce or neutralize) a biological effect that the antigen or receptor has. In various embodiments, the targeting moiety of the present chimeric protein binds an epitope that is physically separate from an antigen site that is important for its biological activity (e.g. an antigen's active site).

Such binding without significant function modulation finds use in various embodiments of the present invention, including methods in which the present chimeric protein is used to directly or indirectly recruit active immune cells to a site of need via an effector antigen. For example, in various embodiments, the present chimeric protein may be used to directly or indirectly recruit dendritic cells (e.g., via XCR1) to a B cell or a tumor cell. In such embodiments, it is desirable to directly or indirectly recruit dendritic cells but not to functionally modulate the XCR1 activity. In these embodiments, XCR1 signaling is an important piece of the tumor reducing or eliminating effect.

Modified Signaling Agent

In one aspect, the present invention provides a chimeric protein that includes a modified signaling agent which has reduced affinity at a therapeutic receptor, which allows for attenuation of activity (inclusive of agonism or antagonism), and/or substantially reduced or ablated affinity at a second receptor, which, for example, prevents non-therapeutic signaling or undesirable sequestration of the chimeric protein.

In various embodiments, the signaling agent is selected from modified versions of cytokines, growth factors, and hormones. Illustrative examples of such cytokines, growth factors, and hormones include, but are not limited to, lymphokines, monokines, traditional polypeptide hormones, such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and tumor necrosis factor-β; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and -II; osteo inductive factors; interferons such as, for example, interferon-α, interferon-β and interferon-γ (and interferon type I, II, and III), colony stimulating factors (CSFs) such as macrophage-CSF (M-CSF); granulocyte-macrophage-CSF (GM-CSF); and granulocyte-CSF (G-CSF); interleukins (ILs) such as, for example, IL-1, IL-1α, IL-2, IL-3, IL-4, IL-5, IL-6, IL-7, IL-8, IL-9, IL-10, IL-11, IL-12, IL-13, and IL-18; a tumor necrosis factor such as, for example, TNF-α or TNF-β; and other polypeptide factors including, for example, LIF and kit ligand (KL). As used herein, cytokines, growth factors, and hormones include proteins obtained from natural sources or produced from recombinant bacterial, eukaryotic or mammalian cell culture systems and biologically active equivalents of the native sequence cytokines.

In some embodiments, the signaling agent is a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon ω.

In various embodiments, the signaling agent is type I interferon that is modified to have one or more mutations. In some embodiments, the mutations allow for the modified signaling agent, i.e., a variant type I interferon, to have one or more of attenuated activity such as one or more of reduced binding affinity, reduced endogenous activity, and reduced specific bioactivity relative to unmutated, e.g., the wild type form of the type I interferon signaling agent. For instance, one or more of attenuated activity such as reduced binding affinity, reduced endogenous activity, and reduced specific bioactivity relative to unmutated, e.g. the wild type form of the type I interferon signaling agent may be at a therapeutic receptor and/or a second receptor. Consequentially, in various embodiments, the mutations allow for the modified signaling agent, i.e., a variant type I interferon, to have reduced systemic toxicity, reduced side effects, and reduced off-target effects relative to unmutated, e.g. the wild type form of the signaling agent.

In various embodiments, the type I interferon signaling agent is modified to have a mutation that reduces its binding affinity or activity at a therapeutic receptor. In some embodiments, the activity provided by the wild type signaling agent, i.e., a type I interferon, is agonism at the therapeutic receptor (e.g. activation of a cellular effect at a site of therapy). For example, the wild type signaling agent, type I interferon, may activate the therapeutic receptor. In such embodiments, the mutations result in the modified signaling agent, i.e., a variant type I interferon, to have reduced activating activity at the therapeutic receptor. In some embodiments, the activity provided by the wild type signaling agent, i.e. a type I interferon, is antagonism at the therapeutic receptor (e.g. blocking or dampening of a cellular effect at a site of therapy). For example, the wild type signaling agent, i.e., a type I interferon, may antagonize or inhibit the therapeutic receptor. In these embodiments, the mutations result in the modified signaling agent, i.e. a variant type I interferon, to have reduced antagonizing activity at the therapeutic receptor. In some embodiments, the reduced affinity or activity at the therapeutic receptor is restorable by attachment with two or more targeting moieties. In other embodiments, the reduced affinity or activity at the therapeutic receptor is not substantially restorable by the activity of the targeting moieties. In various embodiments, the therapeutic chimeric proteins of the present invention reduce off-target effects because their signaling agents have mutations that weaken binding affinity or activity at a therapeutic receptor. In various embodiments, this reduces side effects observed with, for example, the wild type signaling agents. In various embodiments, the modified signaling agent, i.e., a variant type I interferon, is substantially inactive en route to the site of therapeutic activity and has its effect substantially on specifically targeted cell types which greatly reduces undesired side effects.

In various embodiments, the present chimeric proteins also have signaling agents, i.e., a type I interferon, with mutations that substantially reduce or ablate binding or activity at another receptor. This, in some embodiments, further reduces off-target effects of the present chimeric proteins and therefore reduces side effects. In some embodiments, this substantial reduction or ablation of binding or activity is not restorable with a targeting moiety. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss of binding or activity at the other receptor. Such ability to reduce dose further provides a lower likelihood of side effects.

In some embodiments, the chimeric proteins have modified signaling agents, i.e., a variant type I interferon, bearing a mutation that affects interaction with a therapeutic receptor and another receptor (e.g. mediated by the same mutation or multiple mutations). In some embodiments, the present chimeric proteins have a modified signaling agent, i.e., a variant type I interferon, that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative the wild type signaling agent). These mutations may be at the same or at different positions.

In various embodiments, the dual effect at a therapeutic receptor and another receptor can be mediated by the same mutation or multiple mutations. In various embodiments, the mutation(s) that reduce binding and/or activity at a therapeutic receptor is different than the mutation(s) that substantially reduce or ablate at another receptor. In various embodiments, the mutation(s) that reduce binding and/or activity at a therapeutic receptor are the same as the mutation(s) that substantially reduce or ablate at another receptor.

In various embodiments, the modified signaling agent, i.e., a variant type I interferon, comprises one or more mutations that cause the signaling agent to have attenuated or reduced affinity, e.g. binding (e.g. $K_D$) and/or activation (for instance, when the modified signaling agent, i.e., a variant type I interferon, is an agonist at the therapeutic receptor, measurable as, for example, $K_A$ and/or $EC_{50}$) and/or inhibition (for instance, when the modified signaling agent is an antagonist at the therapeutic receptor, measurable as, for example, $K_I$ and/or $IC_{50}$), for one or more therapeutic receptors. In various embodiments, the reduced affinity at the therapeutic receptor allows for attenuation of activity (inclusive of agonism or antagonism). In such embodiments, the modified signaling agent, variant type I interferon, has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the therapeutic receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent, i.e., a type I interferon.

In various embodiments, the modified signaling agent, i.e., a variant type I interferon, comprises one or more mutations that cause the signaling agent to have substantially reduced or ablated affinity, e.g. binding (e.g. $K_D$) and/or activation (for instance, when the modified signaling agent is an agonist at the therapeutic receptor, measurable as, for example, $K_A$ and/or $EC_{50}$) and/or inhibition (for instance, when the modified signaling agent is an antagonist at the therapeutic receptor, measurable as, for example, $K_I$ and/or $IC_{50}$), for one or more other receptors. In such embodiments, the modified signaling agent, i.e., a variant type I interferon, has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the other receptor relative to the wild type signaling agent, type I interferon. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent, i.e., a type I interferon.

In various embodiments, the attenuation or reduction in binding affinity of a modified signaling agent, i.e., a variant type I interferon, for the therapeutic receptor is less than the substantial reduction or ablation in affinity for the other receptor. In some embodiments, the attenuation or reduction in binding affinity of a modified signaling agent, i.e., a variant type I interferon, for the therapeutic receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the modified signaling agent, i.e., a variant type I interferon, comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent, i.e. a type I interferon.

In various embodiments, the modified signaling agent, i.e., a variant type I interferon, comprises one or more mutations that cause the signaling agent to have reduced affinity and/or activity for a receptor of any one of the cytokines, growth factors, and hormones as described herein. In such embodiments, the modified signaling agent, i.e., a variant type I interferon, comprises one or more mutations that cause the signaling agent to have substantially reduced or ablated affinity and/or activity for a different receptor of any one of the cytokines, growth factors, and hormones as described herein.

In some embodiments, the modified signaling agent, i.e., a variant type I interferon, comprises one or more mutations that cause the modified signaling agent, variant type I interferon, to have reduced affinity for a receptor. In some embodiments, the modified signaling agent, variant type I interferon, affinity for a receptor is lower than the binding affinity of the targeting moiety for its receptor. In some embodiments, this binding affinity differential is between the modified signaling agent/receptor and targeting moiety/receptor on the same cell. In some embodiments, this binding affinity differential allows for the modified signaling agent to have localized, on-target effects and to minimize off-target effects that underlie side effects that are observed with wild type signaling agents. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold less.

In an exemplary embodiment, the modified signaling agent is interferon α. In such embodiments, the modified signaling agent has reduced affinity and/or activity for the IFN-α/β receptor (IFNAR) that includes IFNAR1 and IFNAR2 chains. In one embodiment, the modified interferon α has reduced affinity and/or activity at the cell signaling receptor IFNAR1 and substantially reduced or ablated affinity and/or activity at IFNAR2. In one embodiment, the modified interferon α has reduced affinity and/or activity at IFNAR2 and substantially reduced or ablated affinity and/or activity at the cell signaling receptor IFNAR1.

Mutant forms of interferon α are known to the person skilled in the art. In an illustrative embodiment, the modified signaling agent is a variant type I interferon. In this embodiment, the variant type I interferon is human interferon α. In the illustrative embodiment, the variant type I interferon or the allelic form human IFN-α2a having the amino acid sequence of:

```
IFN-α2a (SEQ ID NO: 4):
CDLPQTHSLGSRRTLMLLAQMRKISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE
```

In an illustrative embodiment, the modified signaling agent or the variant type I interferon is the allelic form human IFN-α2b having the amino acid sequence of (which differs from IFN-α2a at amino acid position 23):

```
IFN-α2b (SEQ ID NO: 5):
CDLPQTHSLGSRRTLMLLAQMRRISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE
```

In some embodiments, said IFN-α2 mutant (IFN-α2a or IFN-α2b) is mutated at one or more amino acids at positions 144-154, such as amino acid positions 148, 149 and/or 153. In one embodiment, the variant type I interferon comprises one or more amino acid substitutions at positions 148, 149, and 153 of SEQ ID NO: 4, the substitutions optionally being hydrophobic and selected from alanine, valine, leucine, and isoleucine. In various embodiments, the variant type I interferon (e.g. IFN-α2 mutant) comprises one or more amino acid substitutions at positions 148, 149, and 153 of SEQ ID NO: 4, the substitutions being selected from M148A, R149A, and R153A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In various embodiments, the variant type I interferon has reduced affinity and/or activity at a cell signaling receptor, which is optionally a multisubunit signaling receptor. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wild type IFN-α2 activity. In such embodiments, said mutant IFN-α2 has reduced affinity and/or activity for IFNAR1 while affinity and/or activity of IFNR2 is retained.

In some embodiments, the human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885. In some embodiments, the human IFN-α2 mutant comprises one or more mutations selected from, R144$X_1$, A145$X_2$, and R33A, wherein $X_1$ is selected from A, S, T, Y, L, and I, and wherein $X_2$ is selected from G, H, Y, K, and D.

The amino acid sequences of the wild type signaling agents, i.e., a type I interferon, described herein are well known in the art. Accordingly, in various embodiments the modified signaling agent, i.e., a variant type I interferon, comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any known wild type amino acid sequences of a type I interferon (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified signaling agent, variant type I interferon, comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any of the type I interferon sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified signaling agent, variant type I interferon, comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions as described elsewhere herein.

In various embodiments, the substitutions may also include non-classical amino acids as described elsewhere herein.

Linkers

In some embodiments, the present chimeric protein comprises one or more linkers. In some embodiments, vectors encoding the present chimeric proteins linked as a single nucleotide sequence to any of the linkers described herein are provided and may be used to prepare such chimeric proteins.

In some embodiments, the linker length allows for efficient binding of the two or more targeting moieties and the signaling agent to their targets. For instance, in some embodiments, the linker length allows for efficient binding of one of the targeting moieties and the signaling agent to targets on the same cell as well as the efficient binding of the other targeting moiety to another cell. Illustrative pairs of cells are provided elsewhere herein.

In some embodiments the linker length is at least equal to the minimum distance between the binding sites of one of the targeting moieties and the signaling agent to targets on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to targets on the same cell.

As described herein, the linker length allows for efficient binding of one of the targeting moieties and the signaling agent to targets on the same cell, the binding being sequential, e.g. targeting moiety/target (antigen or receptor) binding preceding signaling agent/receptor binding.

In some embodiments, there are two linkers in a single chimera, each connecting the signaling agent to a targeting moiety. In various embodiments, the modified signaling agent and the two or more targeting moieties are optionally connected with a linker. In various embodiments, the two or more targeting moieties are optionally connected with a linker. In various embodiments, the linkers have lengths that allow for the formation of a site that has a disease cell and an effector cell without steric hindrance that would prevent modulation of the either cell.

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present chimeric protein.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids. In some embodiments, the linker is flexible. In another embodiment, the linker is rigid.

In some embodiments, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids.

In various embodiments, the linker is substantially comprised of alanine, serine and proline repeats. In some embodiments, the linker is a PAS linker. In some embodiments, the PAS linker includes alanine, serine and proline repeats. In some embodiments, said PAS linker is at least about 200 amino acids long or at least about 300 amino acids long. In an embodiment, the PAS linker comprises the amino acid sequence of SEQ ID NO 6:

```
SEQ ID NO 6:
ASPAAPAPASPAAPAPSAPAASPAAPAPASPAAPAPSAPAASPAAPAPAS

PAAPAPSAPAASPAAPAPASPAAPAPSAPAASPAAPAPASPAAPAPSAPA

ASPAAPAPASPAAPAPSAPAASPAAPAPASPAAPAPSAPAASPAAPAPAS

PAAPAPSAPAASPAAPAPASPAAPAPSAPAASPAAPAPASPAAPAPSAPA

ASPAAPAPASPAAPAPSAPAASPAAPAPASPAAPAPSAPAASPAAPAPAS

PAAPAPSAPAASPAAPAPASPAAPAPSAPAASPAAPAPASPAAPAPSAPA
```

In various embodiments, the linker of the invention may comprise a sequence which is at least about 60%, at least about 70%, at least about 80%, at least about 90%, at least about 95%, at least about 96%, at least about 97%, at least about 98%, at least about 99%, or about 100% sequence similarity to SEQ ID NO: 6.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8. In an embodiment, the linker sequence is GGSGGSGGGGSGGGGS. Additional illustrative linkers include, but are not limited to, linkers having the sequence LE, GGGGS, $(GGGGS)_n$ (n=1-4), $(Gly)_8$, $(Gly)_6$, $(EAAAK)_n$ (n=1-3), $A(EAAAK)_nA$ (n=2-5), AEAAAKEAAAKA, $A(EAAAK)_4ALEA(EAAAK)_4A$, PAPAP, KESGSVSSEQLAQFRSLD, EGKSSGSGS-ESKST, GSAGSAAGSGEF, and $(XP)_n$, with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

Production of Chimeric Proteins

Methods for producing the chimeric proteins of the invention are described herein. For example, DNA sequences encoding the chimeric proteins of the invention (e.g., DNA sequences encoding the modified signaling agent and the targeting moiety and the linker) can be chemically synthesized using methods known in the art. Synthetic DNA sequences can be ligated to other appropriate nucleotide sequences, including, e.g., expression control sequences, to produce gene expression constructs encoding the desired chimeric proteins. Accordingly, in various embodiments, the present invention provides for isolated nucleic acids comprising a nucleotide sequence encoding the chimeric protein of the invention.

Nucleic acids encoding the chimeric protein of the invention can be incorporated (ligated) into expression vectors, which can be introduced into host cells through transfection, transformation, or transduction techniques. For example, nucleic acids encoding the chimeric protein of the invention can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the chimeric protein of the invention. Accordingly, in various embodiments, the present invention provides expression vectors comprising nucleic acids that encode the chimeric protein of the invention. In various embodiments, the present invention provides for a recombinant nucleic acid composition encoding one or more of the chimeric proteins of the present invention. In various embodiments, the present invention additional provides host cells comprising such expression vectors. In various embodiments, the present invention provides for a host cell comprising a recombinant nucleic acid composition encoding one or more of the chimeric proteins of the present invention. In some embodiments, the host cell is a prokaryotic or eukaryotic cell.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The chimeric protein of the invention can be produced by growing a host cell transfected with an expression vector encoding the chimeric protein under conditions that permit expression of the protein. Following expression, the protein can be harvested and purified using techniques well known in the art, e.g., affinity tags such as glutathione-S-transferase (GST) and histidine tags or by chromatography.

Accordingly, in various embodiments, the present invention provides for a nucleic acid encoding a chimeric protein of the present invention. In various embodiments, the present invention provides for a host cell comprising a nucleic acid encoding a chimeric protein of the present invention.

Pharmaceutically Acceptable Salts and Excipients

The chimeric proteins described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tertbutylamine, or tris-(hydroxymethyl)methylamine, N,N-dilower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the chimeric proteins described herein and a pharmaceutically acceptable carrier or excipient. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein. In various embodiments, the pharmaceutical formulation is suitable for parenteral administration. In various embodiments, the pharmaceutical formulation is suitable for intravenous administration, intramuscular administration, transdermal administration, or subcutaneous depot administration.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream. In a preferred embodiment, administration of a therapeutically effective amount of a chimeric protein is oral administration, intravenous administration, intramuscular administration, inhalation, rectal administration, vaginal administration, transdermal administration, or subcutaneous depot administration.

In one embodiment, the chimeric protein described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any chimeric proteins described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gel caps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the chimeric protein to be administered according to the present invention will vary according to the particular dosage form, and the mode of administration. Many factors that may modify the action of the chimeric protein (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the chimeric protein is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges therebetween.

Individual doses of the chimeric protein can be administered in unit dosage forms (e.g., tablets or capsules) containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the chimeric protein is administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the chimeric protein is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the invention, the pharmaceutical composition comprising the chimeric protein may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In various embodiments, the pharmaceutical composition of the present invention is co-administered in conjunction with additional therapeutic agent(s). Co-administration can be simultaneous or sequential.

In one embodiment, the additional therapeutic agent and the chimeric protein of the present invention are administered to a subject simultaneously. The term "simultaneously" as used herein, means that the additional therapeutic agent and the chimeric protein are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the chimeric protein can be by simultaneous administration of a single formulation (e.g., a formulation comprising the additional therapeutic agent and the chimeric protein) or of separate formulations (e.g., a first formulation including the additional therapeutic agent and a second formulation including the chimeric protein).

Co-administration does not require the therapeutic agents to be administered simultaneously, if the timing of their administration is such that the pharmacological activities of the additional therapeutic agent and the chimeric protein overlap in time, thereby exerting a combined therapeutic effect. For example, the additional therapeutic agent and the chimeric protein can be administered sequentially. The term "sequentially" as used herein means that the additional therapeutic agent and the chimeric protein are administered with a time separation of more than about 60 minutes. For example, the time between the sequential administration of the additional therapeutic agent and the chimeric protein can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the chimeric protein being administered. Either the additional therapeutic agent or the chimeric protein cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the chimeric protein described herein acts synergistically when co-administered with another therapeutic agent. In such embodiments, the chimeric protein and the additional therapeutic agent may be administered at doses that are lower than the doses employed when the agents are used in the context of monotherapy.

In some embodiments, the present invention pertains to chemotherapeutic agents as additional therapeutic agents.

Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, inclusive, without limitation, of autoimmmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which are incorporated by reference herein.

In some embodiments, inclusive of, without limitation, infectious disease applications, the present invention pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, the present invention pertains to various agents used for treating obesity as additional therapeutic agents. Illustrative agents used for treating obesity include, but are not limited to, orlistat (e.g. ALL1, XENICAL), loracaserin (e.g. BELVIQ), phentermine-topiramate (e.g. QSYMIA), sibutramme (e.g. REDUCTIL or MERJDIA), rimonabant (ACOMPLLA), exenatide (e.g. BYETTA), pramlintide (e.g. SYMLIN) phentermine, benzphetamine, diethylpropion, phendimetrazme, bupropion, and metformin. Agents that interfere with the body's ability to absorb specific nutrients in food are among the additional agents, e.g. orlistat (e.g. ALU, XENICAL), glucomannan, and guar gum. Agents that suppress apetite are also among the additional agents, e.g. catecholamines and their derivatives (such as phenteimine and other amphetamine-based drugs), various antidepressants and mood stabilizers (e.g. bupropion and topiramate), anorectics (e.g. dexedrine, digoxin). Agents that increase the body's metabolism are also among the additional agents.

In some embodiments, additional therapeutic agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; dipcptidyl peptidase 4 (DPP-4) antagonists, agents for treating cardiovascular disease, agents for treating elevated triglyceride levels, agents for treating low HDL, agents for treating hypercholesterolemia, and agents for treating hypertension. Some agents for cardiovascular disease include statins (e.g. lovastatin, atorvastatin, fluvastatin, rosuvastatin, simvastatin and pravastatin) and omega-3 agents (e.g. LOVAZA, EPANQVA, VASCEPA, esterified omega-3's in general, fish oils, krill oils, algal oils). In some embodiments, additional agents may be selected from among amphetamines, benzodiazepines, suifonyl ureas, meglitinides, thiazolidinediones, biguanides, beta-blockers, XCE inhibitors, diuretics, nitrates, calcium channel blockers, phenlermine, sibutramine, iorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, rcpaglinide, nateglinide, glimepiride, metformin, pioglitazone, rosiglilazone, and sitagliptin.

In some embodiments, the present invention pertains to an agent used for treating diabetes as additional therapeutic agents. Illustrative anti-diabetic agents include, but are not limited to, sulfonylurea (e.g., DYMELOR (acetohexamide), DIABINESE (chlorpropamide), ORINASE (tolbutamide), and TOLINASE (tolazamide), GLUCOTROL (glipizide), GLUCOTROL XL (extended release), DIABETA (glyburide), MICRONASE (glyburide), GLYNASE PRESTAB (glyburide), and AMARYL (glimepiride)); a Biguanide (e.g., metformin (GLUCOPHAGE, GLUCOPHAGE XR, RIOMET, FORTAMET, and GLUMETZA)); a thiazolidinedione (e.g. ACTOS (pioglitazone) and AVANDIA (rosiglitazone); an alpha-glucosidase inhibitor (e.g., PRECOSE (acarbose) and GLYSET (miglitol); a Meglitinide (e.g., PRANDIN (repaglinide) and STARLIX (nateglinide)); a Dipeptidyl peptidase IV (DPP-IV) inhibitor (e.g., JANUVIA (sitagliptin), NESINA (alogliptin), ONGLYZA (saxagliptin), and TRADJENTA (linagliptin)); Sodium-glucose cotransporter 2 (SGLT2) inhibitor (e.g. INVOKANA (canaglifozin)); and a combination pill (e.g., GLUCOVANCE, which combines glyburide (a sulfonylurea) and metformin, METAGLIP, which combines glipizide (a sulfonylurea) and metformin, and AVANDAMET, which uses both metformin and rosiglitazone (AVANDIA) in one pill, KAZANO (alogliptin and metformin), OSENI (alogliptin plus pioglitazone), METFORMIN oral, ACTOS oral, BYETTA subcutaneous, JANUVIA oral, WELCHOL oral, JANUMET oral, glipizide oral, glimepiride oral, GLUCOPHAGE oral, LANTUS subcutaneous, glyburide oral, ONGLYZA oral, AMARYI oral, LANTUS SOLOSTAR subcutaneous, BYDUREON subcutaneous, LEVEMIR FLEXPEN subcutaneous, ACTOPLUS MET oral, GLUMETZA oral, TRADJENTA oral, bromocriptine oral, KOMBIGLYZE XR oral, INVOKANA oral, PRANDIN oral, LEVEMIR subcutaneous, PARLODEL oral, pioglitazone oral, NOVOLOG subcutaneous, NOVOLOG FLEXPEN subcutaneous, VICTOZA 2-PAK subcutaneous, HUMALOG subcutaneous, STARLIX oral, FORTAMET oral, GLUCOVANCE oral, GLUCOPHAGE XR oral, NOVOLOG Mix 70-30 FLEXPEN subcutaneous, GLYBURIDE-METFORMIN oral, acarbose oral, SYMLINPEN 60 subcutaneous, GLUCOTROI XL oral, NOVOLIN R inj, GLUCOTROL oral, DUETACT oral, sitagliptin oral, SYMLINPEN 120 subcutaneous, HUMALOG KWIKPEN subcutaneous, JANUMET XR oral, GLIPIZIDE-METFORMIN oral, CYCLOSET oral, HUMALOG MIX 75-25 subcutaneous, nateglinide oral, HUMALOG Mix 75-25 KWIKPEN subcutaneous, HUMULIN 70/30 subcutaneous, PRECOSE oral, APIDRA subcutaneous, Humulin R inj, Jentadueto oral, Victoza 3-Pak subcutaneous, Novolin 70/30 subcutaneous, NOVOLIN N subcutaneous, insulin detemir subcutaneous, glyburide micronized oral, GLYNASE oral, HUMULIN N subcutaneous, insulin glargine subcutaneous, RIOMET oral, pioglitazone-metformin oral, APIDRA SOLOSTAR subcutaneous, insulin lispro subcutaneous, GLYSET oral, HUMULIN 70/30 Pen subcutaneous, colesevelam oral, sitagliptin-metformin oral, DIABETA oral, insulin regular human inj, HUMULIN N Pen subcutaneous, exenatide subcutaneous, HUMALOG Mix 50-50 KWIKPEN subcutaneous, liraglutide subcutaneous, KAZANO oral, repaglinide oral, chlorpropamide oral, insulin aspart subcutaneous, NOVOLOG Mix 70-30 subcutaneous, HUMALOG Mix 50-50 subcutaneous, saxagliptin oral, ACTOPLUS Met XR oral, miglitol oral, NPH insulin human recomb subcutaneous, insulin NPH and regular human subcutaneous, tolazamide oral, mifepristone oral, insulin aspart protam-insulin aspart subcutaneous, repaglinide-metformin oral, saxagliptin-metformin oral, linagliptin-metformin oral, NESINA oral, OSENI oral, tolbutamide oral, insulin lispro protamine and lispro subcutaneous, pramlintide subcutaneous, insulin glulisine subcutaneous, pioglitazone-glimepiride oral, PRANDIMET oral, NOVOLOG PenFill subcutaneous, linagliptin oral, exenatide microspheres subcutaneous, KORLYM oral, alogliptin oral, alogliptin-pioglitazone oral, alogliptin-metformin oral, canagliflozin oral, Lispro (HUMALOG); Aspart (NOVOLOG); Glulisine (APIDRA); Regular (NOVOLIN R or HUMULIN R); NPH (NOVOLIN N or HUMULIN N); Glargine (LANTUS); Detemir (LEVEMIR); HUMULIN or NOVOLIN 70/30; and NOVOLOG Mix 70/30 HUMALOG Mix 75/25 or 50/50.

In some embodiments, the present invention relates to combination therapy with a blood transfusion. For instance, the present compositions may supplement a blood transfusion. In some embodiments, the present invention relates to combination therapy with iron supplements.

In some embodiments, the present invention relates to the use of one or more EPO-based agents as additional therapeutic agents. For example, the present compositions can be used as an adjuvant to other EPO-based agents. In some embodiments, the present compositions are used as a maintenance therapy to other EPO-based agents. Other EPO-based agents include the following: epoetin alfa, including without limitation, DARBEPOETIN (ARANESP), EPOCEPT (LUPIN PHARMA), NANOKINE (NANOGEN PHARMACEUTICAL), EPOFIT (INTAS PHARMA), EPOGEN (AMGEN), EPOGIN, EPREX, (JANSSEN-CILAG), BINOCRIT (SANDOZ), PROCRIT; epoetin beta, including without limitation, NEORECORMON (HOFF-MANN-LA ROCHE), RECORMON, Methoxy polyethylene glycol-epoetin beta (MIRCERA, ROCHE); epoetin delta, including without limitation, DYNEPO (erythropoiesis stimulating protein, SHIRE PLC); epoetin omega, including without limitation, EPOMAX; epoetin zeta, including without limitation, SILAPO (STADA) and RETACRIT (HOSPIRA) and other EPOs, including without limitation, EPOCEPT (LUPIN PHARMACEUTICALS), EPOTRUST (PANACEA BIOTEC LTD), ERYPRO SAFE (BIOCON LTD.), REPOITIN (SERUM INSTITUTE OF INDIA LIMITED), VINTOR (EMCURE PHARMACEUTICALS), EPOFIT (INTAS PHARMA), ERYKINE (INTAS BIOPHARMACEUTICA), WEPOX (WOCKHARDT BIOTECH), ESPOGEN (LG LIFE SCIENCES), RELIPOIETIN (RELIANCE LIFE SCIENCES), SHANPOIETIN (SHANTHA BIOTECHNICS LTD), ZYROP (CADILA HEALTHCARE LTD.), EPIAO (RHUEPO) (SHENYANG SUNSHINE PHARMACEUTICAL CO. LTD), CINNAPOIETIN (CINNAGEN).

In some embodiments, the chimeric protein described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the chimeric protein described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric protein described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials. In an embodiment, the effector moiety is a His tag.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and Pseudomonas toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates, where a radionuclide that emits alpha or beta particles is stably coupled to the chimeric protein, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, autoimmune diseases, cardiovascular diseases, wound healing, ischemia-related diseases, neurodegenerative diseases, metabolic diseases and/or many other diseases and disorders. In various embodiments, the present invention presents a method of treating a disease in a patient, comprising administering to said patient in need thereof a therapeutically effective amount of a chimeric protein of the present invention.

Further, any of the present agents may be for use in the treating, or the manufacture of a medicament for treating, various diseases and disorders, including, but not limited to cancer, infections, immune disorders, inflammatory diseases or conditions, and autoimmune diseases.

In various embodiments, a method of treating a disease in a patient comprises administration of a therapeutically effective amount of a chimeric protein. In one embodiment, administration is parenteral administration. In one embodiment, administration is oral administration, intravenous administration, intramuscular administration, inhalation, rectal administration, vaginal administration, transdermal administration, or subcutaneous depot administration.

In some embodiments, the present invention relates to the treatment of, or a patient having one or more of cancer, heart failure, autoimmune disease, sickle cell disease, thalassemia, blood loss, transfusion reaction, diabetes, vitamin B12 deficiency, collagen vascular disease, Shwachman syndrome, thrombocytopenic purpura, Celiac disease, endocrine deficiency state such as hypothyroidism or Addison's disease, autoimmune disease such as Crohn's Disease, systemic lupus erythematosis, rheumatoid arthritis or juvenile rheumatoid arthritis, ulcerative colitis immune disorders such as eosinophilic fasciitis, hypoimmunoglobulinemia, or thymoma/thymic carcinoma, graft versus host disease, preleukemia, Nonhematologic syndrome (e.g. Down's, Dubowwitz, Seckel), Felty syndrome, hemolytic uremic syndrome, myelodysplasic syndrome, nocturnal paroxysmal hemoglobinuria, osteomyelofibrosis, pancytopenia, pure red-cell aplasia, Schoenlein-Henoch purpura, malaria, protein starvation, menorrhagia, systemic, B-cell lymphoma, rheumatoid arthritis, colitis, diabetes mellitus, or multiple sclerosis.

In some embodiments, the present invention relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In some embodiments, the present invention relates to the treatment of, or a patient having a microbial infection and/or chronic infection. Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In various embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In various embodiments, the present compositions are used to treat or prevent one or more autoimmune diseases or conditions, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In various embodiments, the present compositions are used to treat, control or prevent cardiovascular disease, such as a disease or condition affecting the heart and vasculature, including but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischemic attacks (TIA), angina (stable and unstable), atrial fibrillation, arrhythmia, vavular disease, and/or congestive heart failure.

In various embodiments, the present compositions are used to treat or prevent one or more metabolic-related disorders. In various embodiments, the present invention is useful for the treatment, controlling or prevention of diabetes, including Type 1 and Type 2 diabetes and diabetes associated with obesity. The compositions and methods of the present invention are useful for the treatment or prevention of diabetes-related disorders, including without limitation diabetic nephropathy, hyperglycemia, impaired glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, neoplastic conditions, adipose cell tumors, adipose cell carcinomas, such as liposarcoma, prostate cancer and other cancers, including gastric, breast, bladder and colon cancers, angiogenesis, Alzheimer's disease, psoriasis, high blood pressure, Metabolic Syndrome (e.g. a person has three or more of the following disorders: abdominal obesity, hypertriglyceridemia, low HDL cholesterol, high blood pressure, and high fasting plasma glucose), ovarian hyperandrogenism (polycystic ovary syndrome), and other disorders where insulin resistance is a component, such as sleep apnea. The compositions and methods of the present invention are useful for the treatment, control, or prevention of obesity, including genetic or environmental, and obesity-related disorders. The obesity-related disorders herein are associated with, caused by, or result from obesity. Examples of obesity-related disorders include obesity, diabetes, overeating, binge eating, and bulimia, hypertension, elevated plasma insulin concentrations and insulin resistance, dyslipidemia, hyperlipidemia, endometrial, breast, prostate, kidney and colon cancer, osteoarthritis, obstructive sleep apnea, gallstones, heart disease, abnormal heart rhythms and arrythmias, myocardial infarction, congestive heart failure, coronary heart disease, sudden death, stroke, polycystic ovary disease, craniopharyngioma, Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are Metabolic Syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, lower back pain, gallbladder disease, hyperuricemia, gout, and kidney cancer, and increased anesthetic risk. The compositions and methods of the present invention are also useful to treat Alzheimer's disease.

In various embodiments, the present compositions are used to treat or prevent one or more respiratory diseases, such as asthma, chronic obstructive pulmonary disease (COPD), bronchiectasis, allergic rhinitis, sinusitis, pulmonary vasoconstriction, inflammation, allergies, impeded respiration, respiratory distress syndrome, cystic fibrosis, pulmonary hypertension, pulmonary vasoconstriction, emphysema, Hantavirus pulmonary syndrome (HPS), Loeffler's syndrome, Goodpasture's syndrome, Pleurisy, pneumonitis, pulmonary edema, pulmonary fibrosis, Sarcoidosis, complications associated with respiratory syncitial virus infection, and other respiratory diseases.

In some embodiments, the present invention is used to treat or prevent one or more neurodegenerative disease. Illustrative neurodegenerative disease includes, but are not limited to, multiple sclerosis (including without limitation, benign multiple sclerosis; relapsing-remitting multiple sclerosis (RRMS); secondary progressive multiple sclerosis (SPMS); progressive relapsing multiple sclerosis (PRMS); and primary progressive multiple sclerosis (PPMS)), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In various embodiments, the present chimeric proteins find use in treating wounds, e.g., a non-healing wound, an ulcer, a burn, or frostbite, a chronic or acute wound, open or closed wound, internal or external wound (illustrative external wounds are penetrating and non-penetrating wound. In various embodiments, the present chimeric proteins find use in treating ischemia, by way of non-limiting example, ischemia associated with acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, frostbite, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, or wounds to tissues or organs Kits The invention also provides kits for the administration of any agent described herein (e.g. the chimeric protein with or without various additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired outcome, such as to treat anemia. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

Materials & Methods

As used herein "NB," "Nb," or "nanobody" refers to a variable domain of a camelid heavy chain antibody (VHH). Construction of Plasmid Expressing Vectors Encoding Chimeric Proteins Encompassing mCD20Nb, IFNα2 Mutants and/or mXCL1.

VHH-IFN fusion expression constructs were designed and made in the prokaryotic pHEN6C expression vector using standard recombinant DNA techniques. To allow easy generation of multiple VHH-IFN combinations, a cassette-based master vector was first engineered and termed pHEN6C-NcoI-nanobody-SalI-20*GGS-linker-NotI-IFN-XhoI-His-tag-XbaI. Restriction enzyme-based exchange reactions led to the constructs mCD20NB-20*GGS-hIFNα2_Q124R and mCD20NB-20*GGS-hIFNα2_R149A were used in this study.

VHH-mXCL1-IFN constructs and derivatives were made in the eukaryotic pMET7 expression vector. A fusion protein containing an internal 300*PAS linker (from GeneArt; Life Technologies) was designed as follows: pMET7-EcoRI-SlgK-AgeI-mCD20NB-SalI-300*PAS-PacI-mXCL1-PmeI-5*GGS-NotI-hIFNα2_Q124R-XhoI-His-tag-XbaI, resulting in the mCD20NB-300*PAS-mXCL1-5*GGS-hIFNα2_Q124R-His construct. In the construct mCD20NB-20*GGS-mXCL1-5*GGS-hIFNα2_Q124R-His, the 300*PAS linker was replaced by a 20*GGS linker. Via standard recombinant DNA technology, the hIFNα2_Q124R sequence was removed in both constructs, resulting in mCD20NB-300*PAS-mXCL1-His and mCD20NB-20*GGS-mXCL1-His respectively.

A VHH-mXCL1-IFN construct containing a C-terminal 300*PAS linker was constructed as follows: pMET7-EcoRI-SlgK-AgeI-mCD20NB-SalI-5*GGS-PacI-mXCL1-PmeI-5*GGS-NotI-hIFNα2_Q124R-300*PAS-Xho-His-tag-XbaI, resulting in mCD20NB-5*GGS-mXCL1-5*GGS-hIFNα2_Q124R-300*PAS-His.

Finally, the construct mXCL1-20*GGS-hIFNα2_Q124R-His was made as follows: pMET7-EcoRI-SlgK-mXCL1-SalI-20*GGS-NotI-hIFNα2_Q124R-XhoI-His-tag-XbaI.

Production of the VHH-IFN and VHH-mXCL1-IFN Fusion Proteins

VHH-IFN fusion proteins: E. coli WK6 cells were stably transformed with the protein fusion vectors using the KCM buffer (0.5 M KCl, 0.15 M CaCl$_2$, 0.25 M MgCl$_2$). Overnight pre-cultures were added 1 over 330 to Terrific Broth medium and grown till an OD$_{600}$ of 0.6-0.9 was reached. Protein expression was induced by addition of IPTG to a final concentration of 1 mM, and the culture was further grown overnight at 28° C. with shaking. Cells were harvested by centrifugation and periplasmic extracts prepared using a TES buffer (30 mM Tris-HCl, 1 mM EDTA, 20% Sucrose).

VHH-mXCL1-IFN fusion proteins were produced in FreeStyle 293-F cells in FreeStyle 293 Expression Medium (both Invitrogen, Life Technologies) by transient transfection with PEIpro (Polyplus transfection) according to the manufacturer's guidelines. Four days after transfection, medium was collected, centrifuged and filtered.

Fusion proteins were purified from periplasmic extracts (VHH-IFN) or conditioned medium (VHH-mXCL1-IFN) with the Ni Sepharose High Performance (GE Healthcare Life Sciences, Cat#17-5268-01) by gravity flow. Imidazol used for elution was removed with PD-10 desalting columns (GE Healthcare Life Sciences, Cat#17-0851-01). Protein concentrations were measured using the NanoDrop spectrophotometer (Thermo Scientific) and purity analyzed on SDS-PAGE. LPS contamination were assessed by a chromogenic Limulus Amoebocyte Lysate Assay (Lonza, Cat#50-647U) and removed, if needed, with Polymyxin B-Agarose (Sigma-Aldrich Cat#P1411).

An overview of the different chimeric proteins used is given in the table below:

| Compound Code | Chimeric protein |
|---|---|
| 9735 | mCD20NB-20GGS-IFNα2Q124R-His |
| 9737 | mXCL1-20GGS-IFNα2Q124R-His |
| 10056 | mCD20NB-5xggs/mXCL1/5xggs-IFNα2Q124R-300PAS-his |
| 10058 | mCD20NB-300PAS-mXCL1/5xggs-IFNα2Q124R-his |
| 10121 | mCD20NB-20xggs-IFNα2R149A-his |
| 10339 | mCD20NB-20xggs-mXCL1-5xggs-IFNα2Q124R-his |
| 10340 | mCD20NB-20xggs-mXCL1-his |
| 10341 | mCD20NB-300PAS-mXCL1-his |

Mice

Balb/c and C57Bl6 mice were obtained from Harlan. IFNAR1 KO C57Bl6 mice are a generous gift from M. Alberts (Institut Pasteur, Paris).

Mouse B Cells Purification

Splenocytes from mouse Balb/c were recovered and B cells were isolated using mouse B cell isolation kit (StemCell #19854) according to manufacturer's recommendations.

FACS Analysis of CD19 Expressing Cells

Cells (splenocytes or purified mouse B cells) were plated on culture cell plates, treated or not with the indicated compounds for 30 minutes at 37° C. They were recovered by scraping using a policeman (CytoOne). Cells were then labelled with the APC-labelled rat anti-mouse CD19 (BD 550992). FACS data were acquired in the viable cellular subpopulation using BD FACS Canto. Data were analyzed using Diva (BD Biosciences).

Phospho STAT1 Assay in Splenocytes

Single-cell suspensions were prepared from spleens. Erythrocytes were depleted using red blood cell lysis buffer (Lonza). Isolated splenocytes were treated or not for 30 min with the indicated constructs or murine IFNα/in RPMI 5% fetal calf serum at 37° C. Cells were then scraped, fixed, permeabilized and labelled with the BD Phosflow PE mouse anti-STAT1 (pY701) (BD 612564) together with either the APC-labelled rat anti-mouse CD19 (BD 550992) or the APC-labelled rat anti-mouse CD8α (BD 553035) and the Alexa488-labelled armenian hamster anti-mouse CD11c (eBioscience 53-0114-82) according to BD Biosciences instructions.

Binding of Compounds 10056 and 10058

Binding studies were done on the A20 mouse B cell line. Cells ($1 \cdot 10^6$) were treated with compound 10056 or 10058 at different concentration (3, 1, 0.1, 0.01 μg/ml) for 1 hour 30 minutes at 4° C. After two washes with PBS 1% SVF 0.09% NaN3 buffer, cells were incubated for 40 minutes at 4° C. with 1 μg/ml of anti-His-FITC (GenScript A01620). Cells were then washed two times with PBS 1% SVF 0.09% NaN3 buffer before being analyzed using a BD FACS Canto and Diva software (BD Biosciences).

Microscopy

A20 cells were plated in 24-well plates or in CELLview Glass Bottom Dish (Greiner bio-one 627 870) and treated or not with 2 μg/ml of compound 10341. Cells were imaged 4 to 18 hours later using either the Spinning Disk CSU-W1 (×20 ocular zoom+×1.5 numerical zoom; for cells in 24-well plates) or the Axiovert 200M Zeiss Inverted microscope (×40; for cells in CELLview Glass Bottom Dish). Images were analyzed using ImageJ freeware.

In Vivo Activity of mCD20nb-mXCl1 Compounds

The compounds were injected intravenously in Balb/c, C57Bl6 or IFNAR1 KO C57Bl6 mice. Peripheral blood was collected 10 minutes, 30 minutes, 4 hours or 24 hours later in heparin coated tube and cells were labelled with the APC-labelled rat anti-mouse CD19 (BD 550992) for 30 minutes at room temperature. BD FACS lysing solution (BD 349202) was then added on sample in order to lyse red blood cells and fix other cells. FACS data were acquired using a BD FACS Canto and analyzed using Diva (BD Biosciences).

Figure 1B:
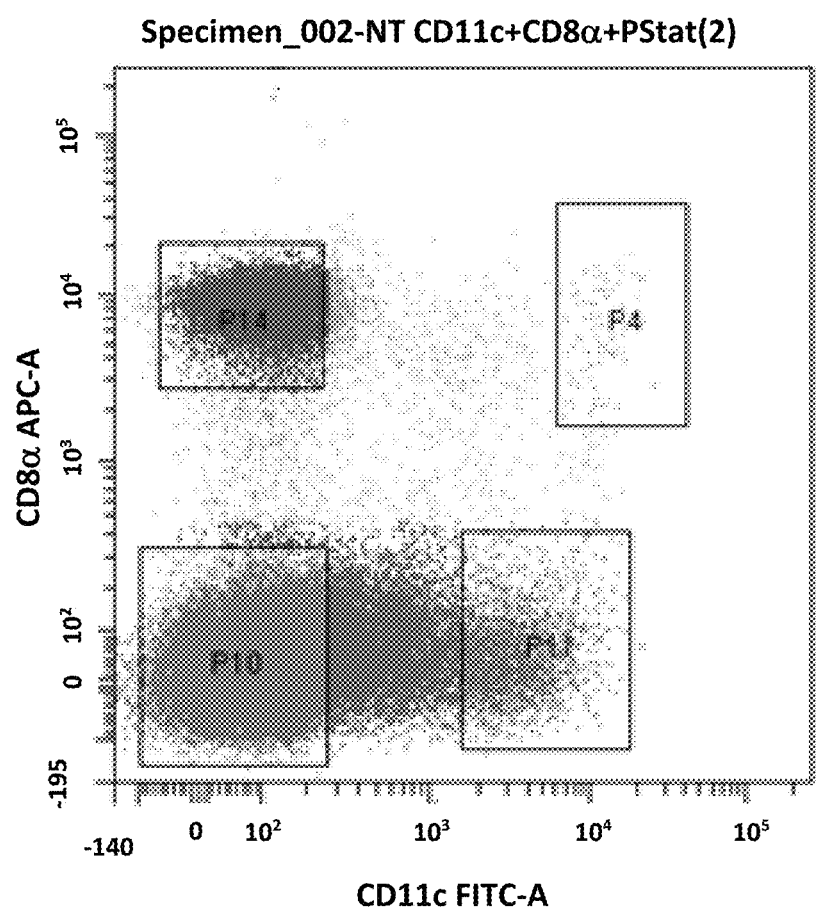
Figure 1C:
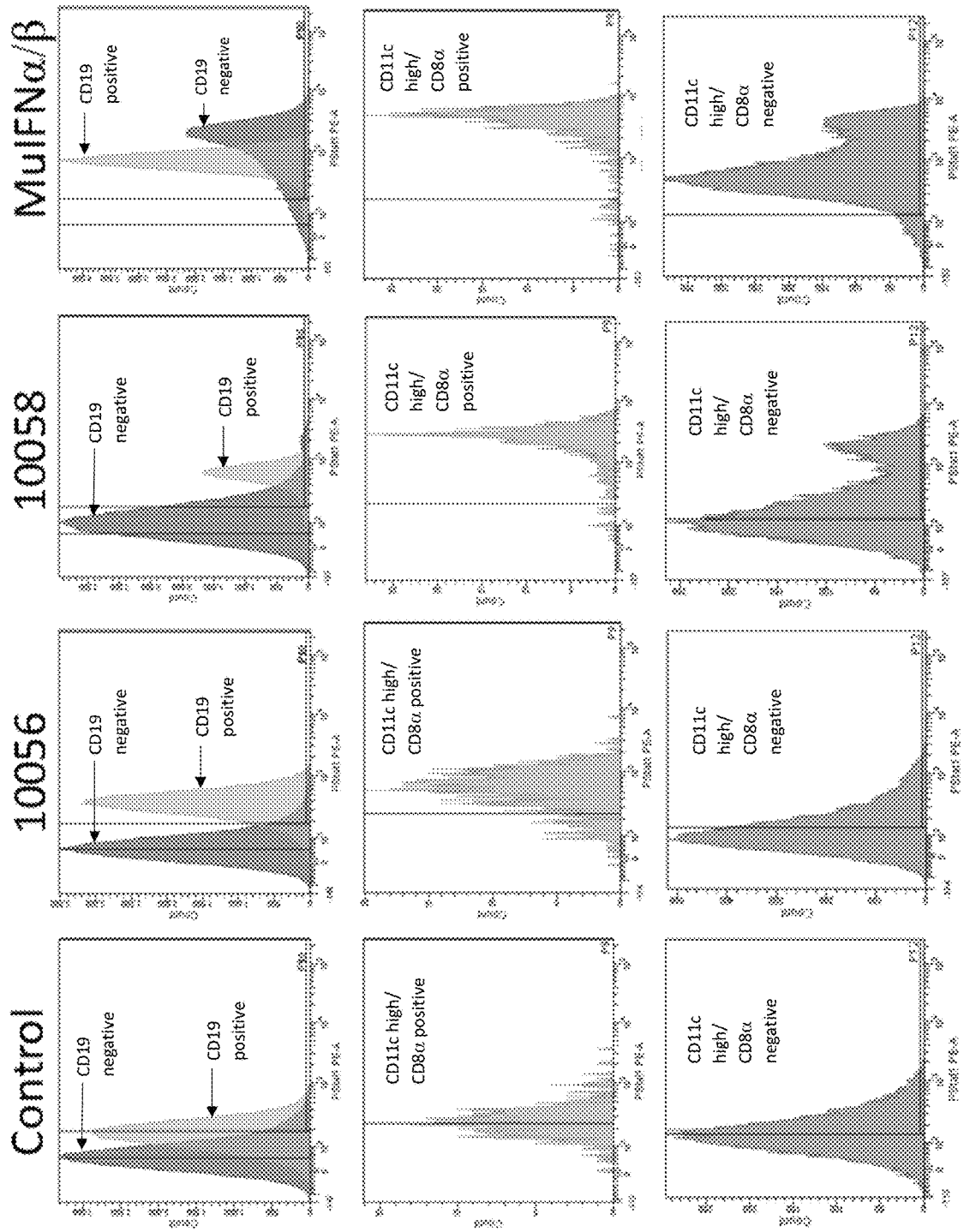
FIG. 1C shows the level of Stat1 phosphorylation in CD19 positive (orange), CD19 negative (purple), CD11c high/CD8α positive (blue) or CD11c high/ CD8α negative (green) cell populations using PE-labelled anti-Stat1 (pY701) antibody together with CD19 or CD11c CD8α antibodies.

Example 1: Activity of mCD20nb-mXCL1-IFNα2Q124R Constructs on Mouse Splenocytes mCD20nb-300PAS-mXCL1/5xggs-IFNα2Q124R-his (compound 10058) and mCD20nb-5xggs/mXCL1/5xggs-IFNα2Q124R-300PAS-his (compound 10056) were designed in order to target IFN activity on both B cells expressing CD20 and dendritic cells expressing XCR1. The activities of compound 10056 and 10058 were evaluated ex vivo on mouse Balb/c splenocytes by analysing the induction of Stat1 phosphorylation. In spleen, all CD20+ cells express also CD19, and CD19 positive cells represented about 50% of total lymphocytes (Balb/c mice). XCR1 was expressed in 70-85% of CD8α positive dendritic cells (DC) and in 2-8% of CD8α negative DCs (Dorner et al. 2009). FIG. 1 shows that both 10058 and 10056 induced IFN activity specifically in mouse CD19/CD20 positive and CD11c high/CD8α+ cells, however at a lower extent for compound 10056. Only 10058 induced IFN activity in a fraction of CD11c high/CD8α− cells. Thus, at same dose, compound 10058 was more efficient than 10056 for inducing Stat1 phosphorylation.

Figure 2:
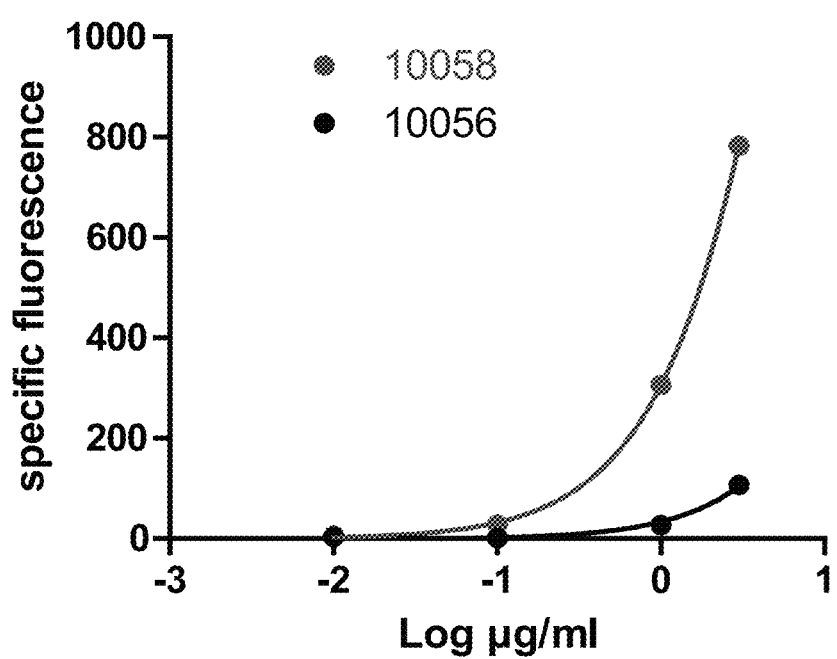
FIG. 2. Binding of compounds 10056 and 10058 on A20 cells. A20 B cells were incubated with various concentrations of 10056 or 10058 for 1 hour 30 minutes at 4° C. After extensive wash, cells were incubated with anti-His-FITC secondary antibody for 40 minutes at 4° C. Cells were then analyzed by FACS. Curves were obtained using GraphPad Prism, by plotting the specific fluorescence as a function of compound concentration (expressed as log). Specific fluorescence was obtained by subtracting the mean fluorescence of non-treated cells incubated with secondary antibody to the mean fluorescence of treated cells. Top curve is compound 10058 and bottom curve is compound 10056.

By measuring the binding of 10056 and 10058 on the A20 B cell line, it was demonstrated that 10058 bound cells with higher efficiency than 10056 (FIG. 2).

Example 2: Compound 10058 Induces Adherence of B Cells

Figure 3A:
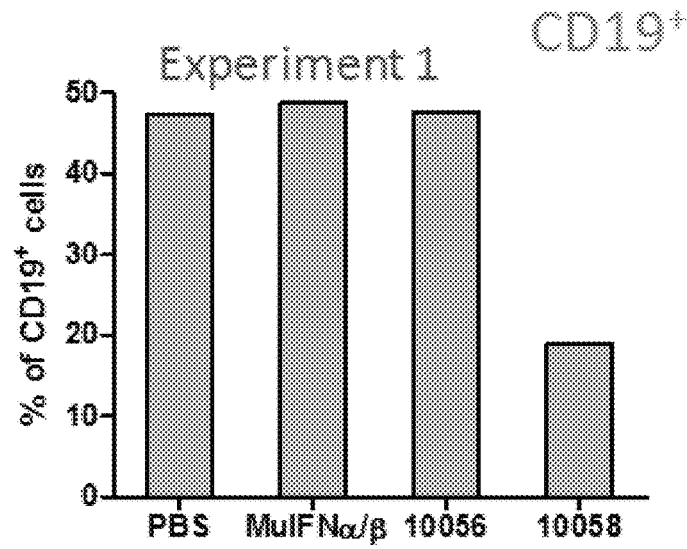
FIGS. 3A-D. Compound 10058 induced a decrease in CD19/CD20 positive cell number. Mouse Balb/c splenocytes were treated with compound 10058 (2 µg/ml), 10056 (2 µg/ml), 9735 (2 µg/ml) or MuIFNα/b (10000 U/ml) for 30 minutes at 37° C. Cells treated with PBS served as negative controls. Cells were then scraped and labelled with anti-CD19 (FIGS. 3A-B) or anti-CD11c and anti-CD8α antibodies (FIGS. 3C-D). The percentage of labelled cells is determined in the viable cell subpopulations.
Figure 3B:
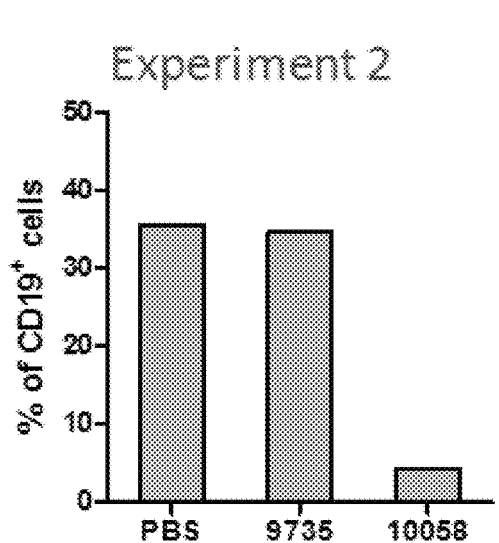
Figure 3C:
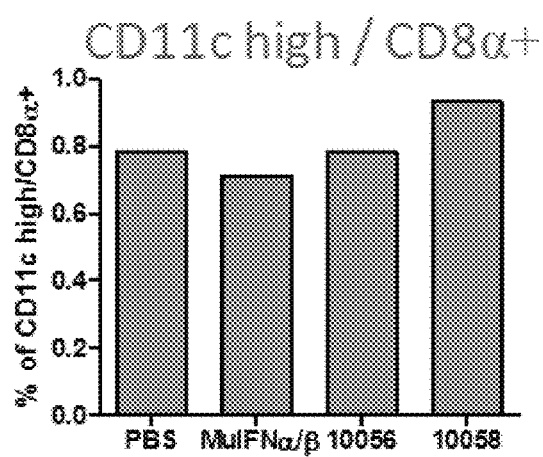
Figure 3D:
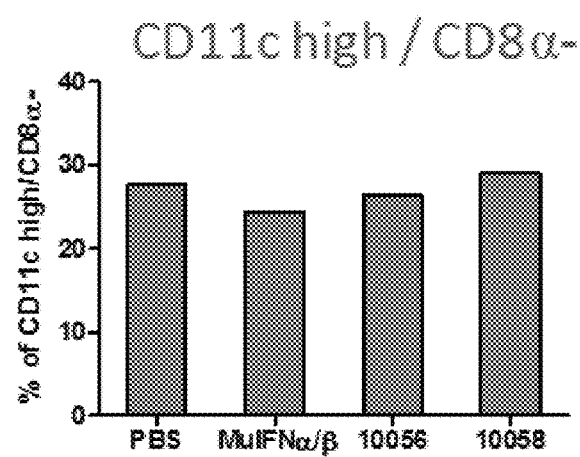

In addition to IFN-induced activities, 10058 but not 10056 or 9735 reduced the number of viable CD19+ cells when splenocytes were scraped from culture dishes (FIGS. 1A-C and FIGS. 3A-B). Such an effect was not observed for CD11c high/CD8α positive and CD11c high/CD8α negative population (FIGS. 3C-D).

Visual observation indicated that 10058 induced the adherence of a subpopulation of splenocytes on the culture dish surface. Trypan blue staining indicated that these cells were alive when attached but dead when scraped. These cells were probably the CD19/CD20 positive cells as a decrease in this population was previously shown by FACS upon 10058 treatment (FIGS. 3A-D).

Figure 4:
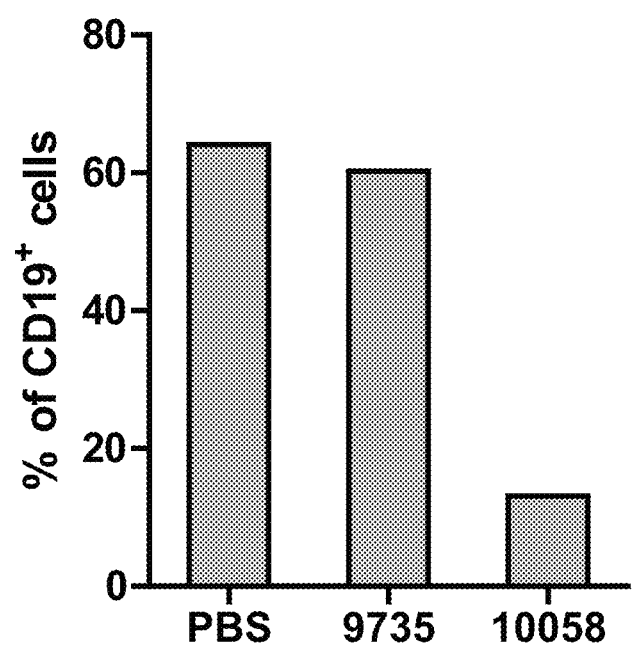
FIG. 4. Compound 10058 induced adherence of purified B cells. B cells were purified from Balb/c splenocytes using a negative selection StemCell kit and treated with compound 10058 (2 µg/ml) or 9735 (2 µg/ml) for 30 minutes at 37° C. Cells treated with PBS served as negative controls. Cells were then scraped and labelled with anti-CD19 antibody and analyzed by FACS analysis.

Adherence of CD19/CD20 positive cells induced by compound 10058 did not require any other cellular subtype contribution as a similar effect was observed on purified B cells (FIG. 4).

Figure 5A:
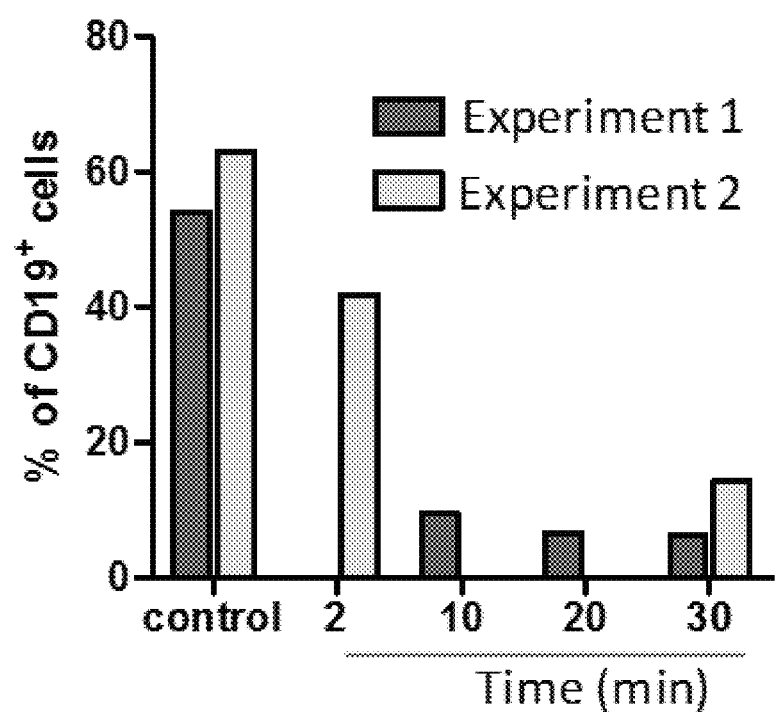
FIGS. 5A-B. Kinetics of activity of compound 10058. Balb/c splenocytes were treated with compound 10058 at 2 µg/ml (FIG. 5A) or 200 ng/ml (FIG. 5B) for 2 to 120 minutes at 37° C. Cells treated with PBS served as negative controls. Cells were then scraped, labelled with anti-CD19 antibody and analyzed by FACS analysis.
Figure 5B:
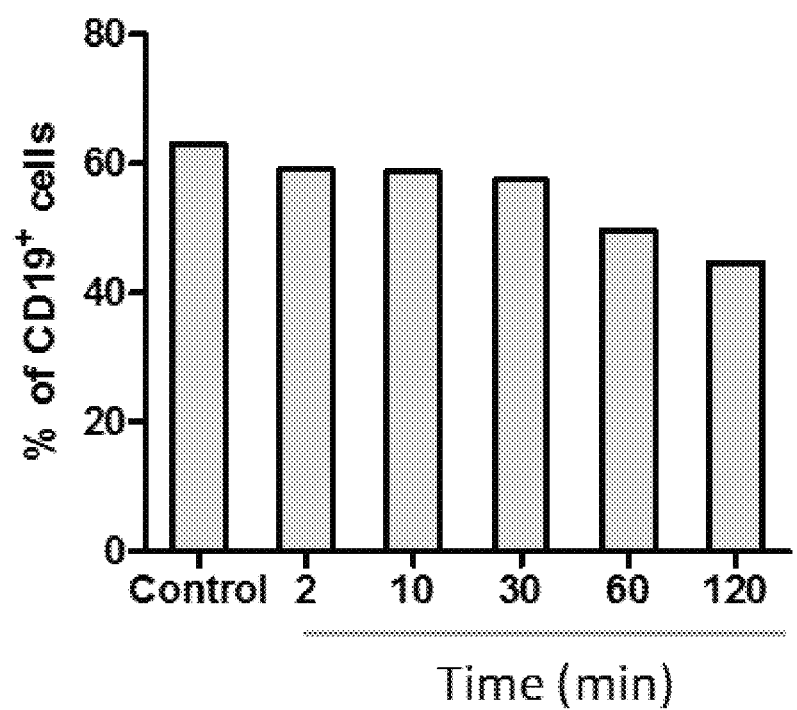

Adherence occurred very rapidly, as fast as 10 minutes at a concentration of 2 μg/ml of 10058 (FIG. 5A). At lower doses, such as 200 ng/ml, no decrease in CD19/CD20 positive cells was observed within 1 hour (FIG. 5B).

Example 3: The Adherence Mechanism does not Require IFN Signalling but Depends on Both the Anti-CD20 VHH and XCL1

Figure 6:
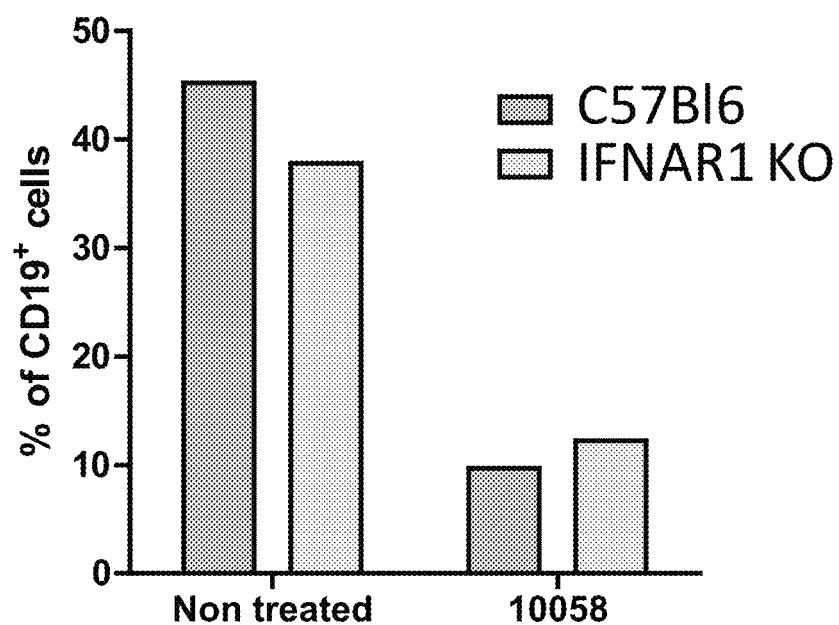
FIG. 6. IFN signalling was not required for adherence induction. B cells from C57Bl6 or C57Bl6 IFNAR1 KO mice were purified by negative selection (StemCell) and treated with compound 10058 (2 µg/ml) for 30 minutes at 37° C. Cells treated with PBS served as negative controls. Cells were then scraped, labelled with anti-CD19 antibody and analyzed by FACS analysis.

The adherence mechanism did not require IFN signalling since cell adherence was also induced by compound 10058 in B cells isolated from IFNAR1 KO mice (FIG. 6) and by compound 10341 in A20 cells (FIGS. 7A-D). Compound 10341 was a protein made by the fusion of the anti-CD20 VHH with XCL1 but without IFNα2Q124R (mCD20nb-300PAS-mXCL1-his).

Figure 8A:
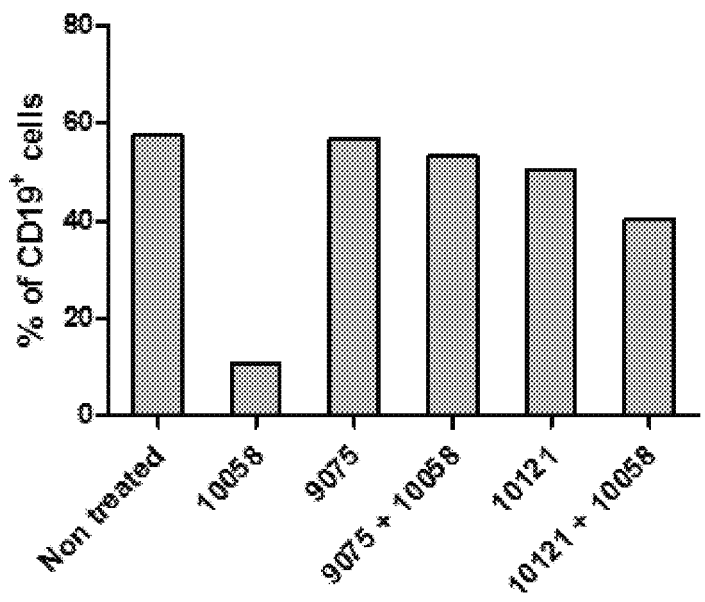
FIGS. 8A-C. Adherence effect was reversed by an excess of unconjugated variable domain of a camelid heavy chain antibody (VHH) or XCL1.
Figure 8B:
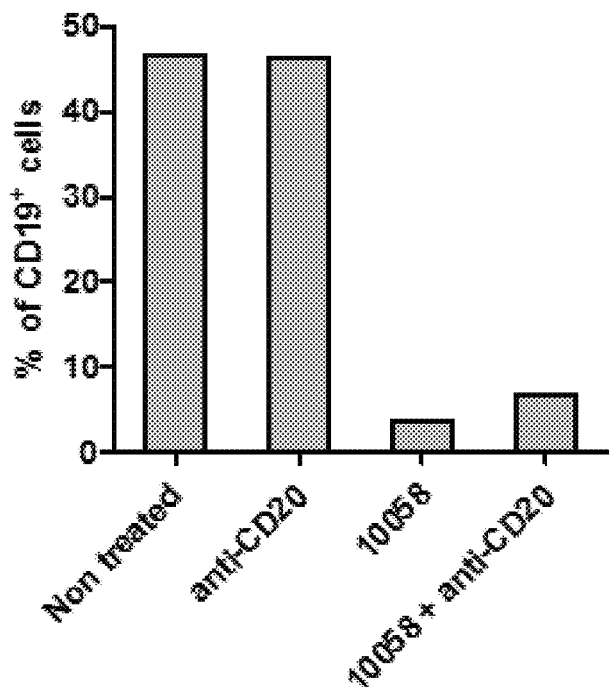
Figure 8C:
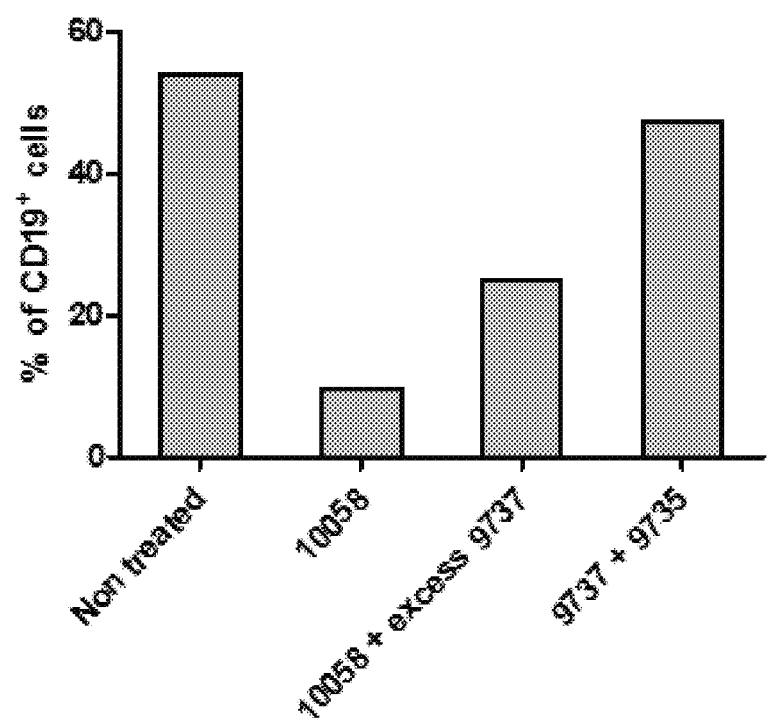

Binding of 10058 via the mouse CD20 VHH was required for adherence of cells since preincubation of splenocytes with an excess of unconjugated VHH before stimulation with compound 10058 reversed this adherence effect (FIG. 8A). A similar effect was obtained with compound 10121 which was a fusion between the anti-CD20 VHH and IFNα2R149A (totally inactive in mouse) (FIG. 8A). In contrast, a commercial anti-CD20 antibody was unable to reverse the adherence effect induced by compound 10058 (FIG. 8B). Incubation of splenocytes with an excess of compound 9737, which was a fusion between mouse XCL1 and IFNα2Q124R, also partially reversed cell adherence (FIG. 8C). Treatment of cells with a combination of compounds 9737 (mXCL1-20GGS-IFNQα2124R-His) and 9735 (mCD20Nb-20GGS-IFNα2Q124R-6His) did not have any effect (FIG. 8C).

Altogether these results indicated that both the anti-CD20 VHH and XCL1 but not the IFNα2Q124R part of the construct 10058 were necessary to initiate adherence of B cells. They also showed that both the anti-CD20 Nb and XCL1 modules must be physically linked to induce B cell adherence.

Figure 9A:
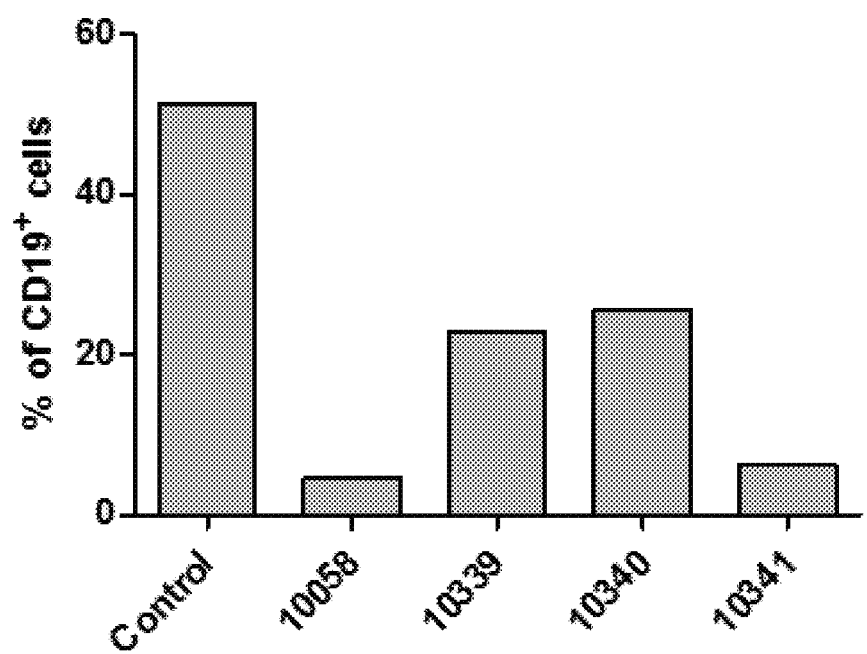
FIGS. 9A-B. The 300 amino acid PAS linker sequence in the fusion protein enhanced adherence induction. Balb/c splenocytes (FIG. 9A) or purified B cells (FIG. 9B) were treated with compounds 10058 (2 µg/ml), 10339, 10340 and 10341 (same molarity as 10058) for 30 minutes at 37° C. Cells were then scraped, labelled with anti-CD19 antibody and analyzed by FACS analysis.
Figure 9B:
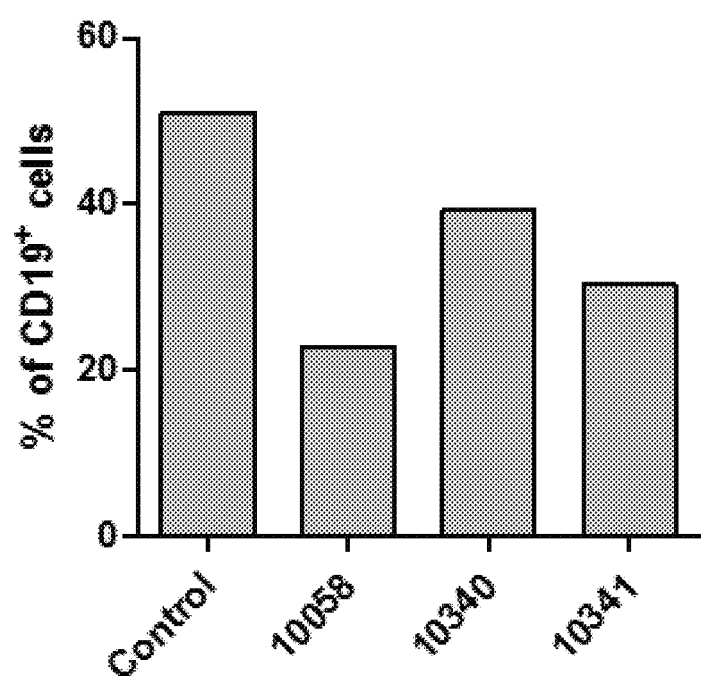

Example 4: The 300 PAS Linker Sequence in the Fusion Protein Enhances Adherence Induction In order to evaluate the importance of the 300PAS linker motif, new constructs were made in which the 300PAS sequence was replaced by a 20GGS sequence (compounds 10339 and 10340). For some fusion proteins, IFNα2Q124R was also removed (compounds 10340 and 10341). Those constructs were first tested ex vivo on mouse splenocytes or purified B cells. As can be seen in FIGS. 9A-B, compounds 10339 and 10340 were less efficient than 10058 in inducing cell adherence. In contrast, compound 10341 which contained the 300PAS linker but not the IFNα2Q124R module appears as efficient as compound 10058 (FIG. 9A).

Figure 10:
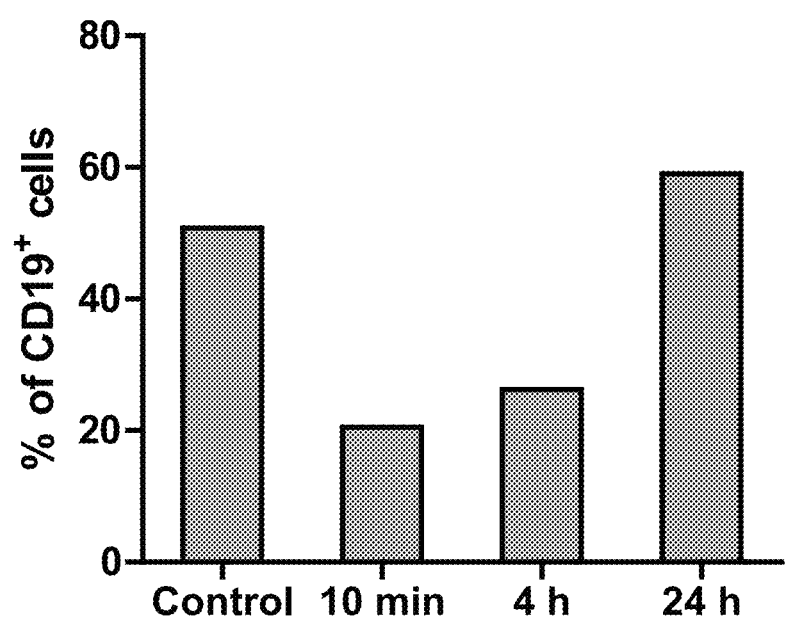
FIG. 10. Compound 10058 induced a rapid decrease in peripheral CD19/CD20 positive blood cells. Compound 10058 (25 µg) was injected intravenously in IFNAR1 KO mice and sample of peripheral blood were collected 10 minutes, 4 hours or 24 hours later. Cells were labelled with CD19 antibody and analyzed by FACS analysis.

Example 5: Compounds 10058 and 10341 Induce a Strong Decrease in Circulating B Cells when Injected in Mice In order to evaluate the in vivo effects, compounds were injected intravenously in mice and peripheral blood was recovered few minutes or several hours later for determining the percentage of CD19/CD20 positive cells by flow cytometry. FIG. 10 shows that compound 10058 induced a decrease of circulating CD19/CD20 positive cells 10 minutes after injection. The percentage of CD19/CD20 positive cell returned to a normal level 24 hours after injection (FIG. 10).

Figure 11:
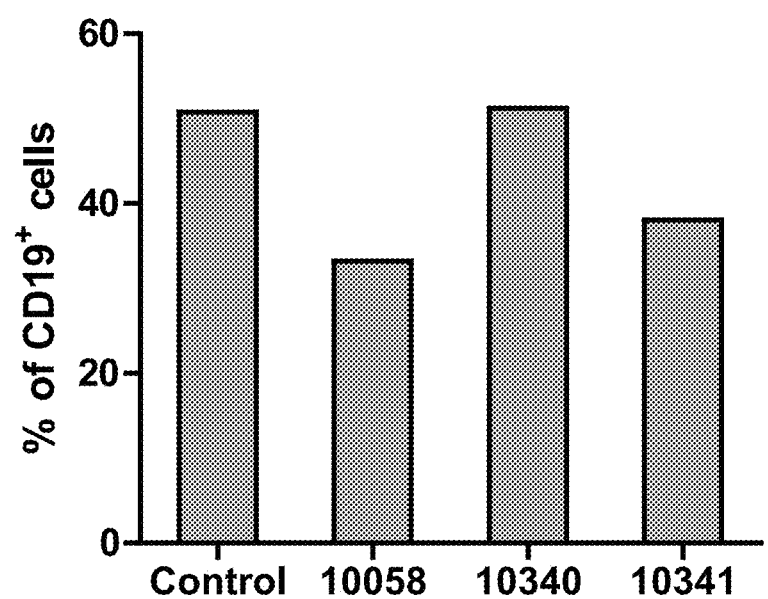
FIG. 11. Compound 10341 but not 10340 was as efficient as compound 10058 in vivo. Compound 10058 (10 µg), 10341 (10 µg) and 10340 (8 µg) were injected intravenously into IFNAR1 KO mice. Sample of peripheral blood were collected 30 minutes later. Cells were labelled with CD19 antibody and analyzed by FACS.

As was observed in ex vivo experiments, compound 10341 was more efficient than 10340 (FIG. 11), suggesting that the 300PAS motif was important for this effect.

Figure 12A:
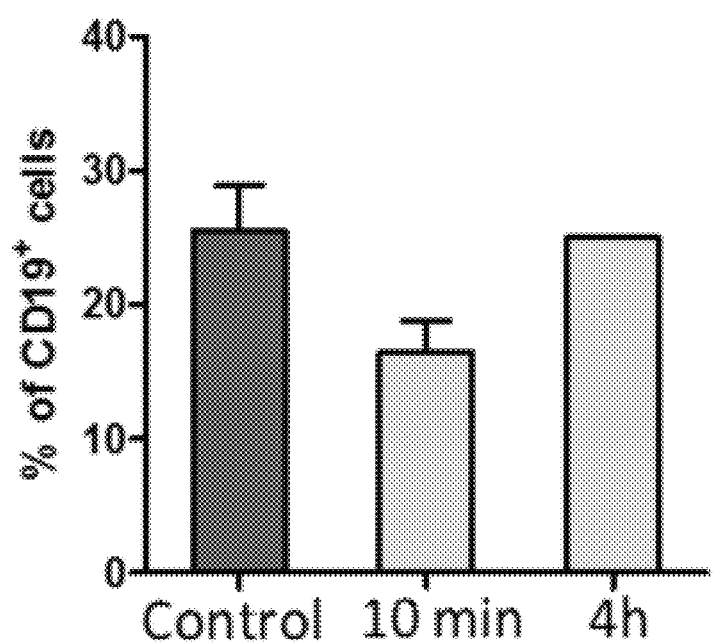
FIGS. 12A-B. In vivo activity of compound 10341.
Figure 12B:
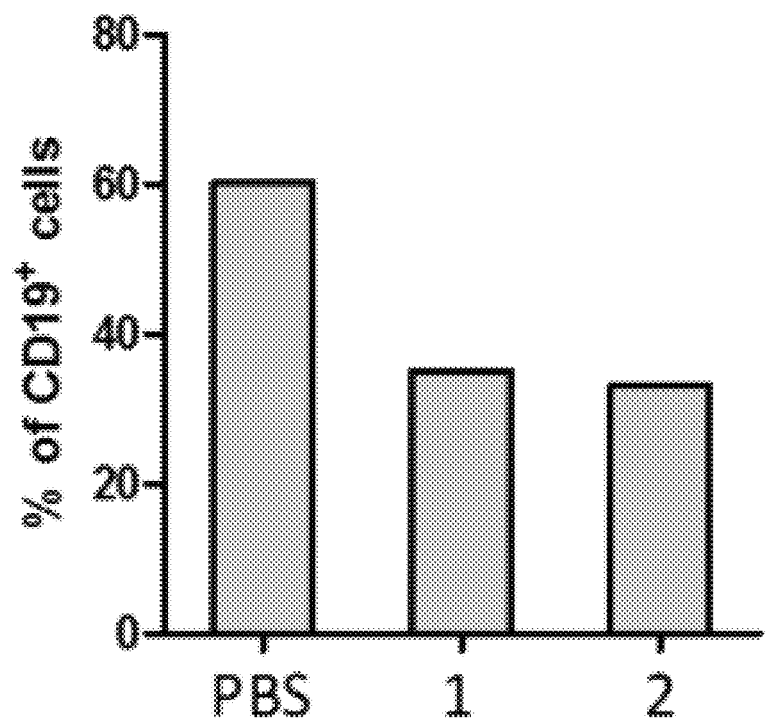

Compound 10341, as 10058, induced a decrease in circulating CD19/CD20 positive cells as fast as 10 minutes after injection. The same effect was also noted in mice having received a second injection 24 hours after the first one. (FIGS. 12A-B).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

---

What is claimed is:

1. A chimeric protein comprising:
   (a) two or more targeting moieties, the targeting moieties comprising recognition domains which specifically bind to antigens of interest, wherein:
      (i) a first targeting moiety is a single-domain antibody directed against CD20, and
      (ii) a second targeting moiety is Chemokine (C motif) ligand (XCL1); and
   (b) a modified human interferon alpha 2, having at least 95% identity with SEQ ID NO: 4 and having one or more amino acid substitutions at positions 144-154, or positions corresponding thereto, that confer a reduced affinity or activity for its receptor relative to the wild type human interferon alpha 2,
   wherein the reduced affinity or activity of the modified human interferon alpha 2 for its receptor is restorable by one or more of the targeting moieties.

2. The chimeric protein of claim 1, wherein the human interferon alpha 2 comprises one or more amino acid substitutions at positions 148, 149, and 153 of SEQ ID NO: 4, or positions corresponding thereto, the substitutions being selected from alanine, valine, leucine, and isoleucine.

3. The chimeric protein of claim 2, wherein substitutions are selected from M148A, R149A, and R153A.

4. The chimeric protein of claim 1, wherein the receptor is a Type I interferon receptor (IFNAR1).

5. The chimeric protein of claim 1, wherein the single-domain antibody is a recombinant heavy-chain-only antibody (VHH), a single-chain antibody (scFv), or a shark heavy-chain-only antibody (VNAR).

6. The chimeric protein of claim 5, wherein the single-domain antibody is a recombinant heavy chain antibody ($V_{HH}$) or a shark heavy-chain-only antibody (VNAR).

7. The chimeric protein of claim 6, wherein the single-domain antibody is a $V_{HH}$ or a humanized $V_{HH}$.

8. The chimeric protein of claim 7, wherein the single-domain antibody is a recombinant heavy chain antibody ($V_{HH}$) that specifically binds to CD20.

9. The chimeric protein of claim 1, wherein the modified human interferon alpha 2 and the two or more targeting moieties are connected with a linker.

10. The chimeric protein of claim 9, wherein the linker connects the N-terminus and/or the C-terminus of the modified human interferon alpha 2 to the two or more targeting moieties.

11. The chimeric protein of claim 9, wherein the linker connects the modified human interferon alpha 2 and targeting moieties in an orientation in which the modified human interferon alpha 2 is adjacent to at least two targeting moieties.

12. The chimeric protein of claim 1, wherein the two or more targeting moieties are connected with a linker.

13. The chimeric protein of claim 12, wherein the linker connects the N-terminus and/or the C-terminus of the two or more targeting moieties to each other.

14. A method of treating a disease in a patient, comprising administering to said patient in need thereof a therapeutically effective amount of a chimeric protein claim 1, wherein said disease is cancer or an autoimmune disease or disorder.

* * * * *

SEQUENCE LISTING

```
<160> NUMBER OF SEQ ID NOS: 6

<210> SEQ ID NO 1
<211> LENGTH: 297
<212> TYPE: PRT
<213> ORGANISM: Homo sapiens

<400> SEQUENCE: 1

Met Thr Thr Pro Arg Asn Ser Val Asn Gly Thr Phe Pro Ala Glu Pro
1               5                   10                  15
```

```
Met Lys Gly Pro Ile Ala Met Gln Ser Gly Lys Pro Leu Phe Arg
             20                  25                  30
Arg Met Ser Ser Leu Val Gly Pro Thr Gln Ser Phe Phe Met Arg Glu
         35                  40                  45
Ser Lys Thr Leu Gly Ala Val Gln Ile Met Asn Gly Leu Phe His Ile
     50                  55                  60
Ala Leu Gly Gly Leu Leu Met Ile Pro Ala Gly Ile Tyr Ala Pro Ile
65                  70                  75                  80
Cys Val Thr Val Trp Tyr Pro Leu Trp Gly Gly Ile Met Tyr Ile Ile
                 85                  90                  95
Ser Gly Ser Leu Leu Ala Ala Thr Glu Lys Asn Ser Arg Lys Cys Leu
            100                 105                 110
Val Lys Gly Lys Met Ile Met Asn Ser Leu Ser Leu Phe Ala Ala Ile
        115                 120                 125
Ser Gly Met Ile Leu Ser Ile Met Asp Ile Leu Asn Ile Lys Ile Ser
    130                 135                 140
His Phe Leu Lys Met Glu Ser Leu Asn Phe Ile Arg Ala His Thr Pro
145                 150                 155                 160
Tyr Ile Asn Ile Tyr Asn Cys Glu Pro Ala Asn Pro Ser Glu Lys Asn
                165                 170                 175
Ser Pro Ser Thr Gln Tyr Cys Tyr Ser Ile Gln Ser Leu Phe Leu Gly
            180                 185                 190
Ile Leu Ser Val Met Leu Ile Phe Ala Phe Phe Gln Glu Leu Val Ile
        195                 200                 205
Ala Gly Ile Val Glu Asn Glu Trp Lys Arg Thr Cys Ser Arg Pro Lys
    210                 215                 220
Ser Asn Ile Val Leu Leu Ser Ala Glu Glu Lys Lys Glu Gln Thr Ile
225                 230                 235                 240
Glu Ile Lys Glu Glu Val Val Gly Leu Thr Glu Thr Ser Ser Gln Pro
                245                 250                 255
Lys Asn Glu Glu Asp Ile Glu Ile Ile Pro Ile Gln Glu Glu Glu Glu
            260                 265                 270
Glu Glu Thr Glu Thr Asn Phe Pro Glu Pro Pro Gln Asp Gln Glu Ser
        275                 280                 285
Ser Pro Ile Glu Asn Asp Ser Ser Pro
    290                 295

<210> SEQ ID NO 2
<211> LENGTH: 333
<212> TYPE: PRT
<213> ORGANISM: Homo sapiens

<400> SEQUENCE: 2

Met Glu Ser Ser Gly Asn Pro Glu Ser Thr Thr Phe Phe Tyr Tyr Asp
1               5                   10                  15
Leu Gln Ser Gln Pro Cys Glu Asn Gln Ala Trp Val Phe Ala Thr Leu
            20                  25                  30
Ala Thr Thr Val Leu Tyr Cys Leu Val Phe Leu Leu Ser Leu Val Gly
        35                  40                  45
Asn Ser Leu Val Leu Trp Val Leu Val Lys Tyr Glu Ser Leu Glu Ser
    50                  55                  60
Leu Thr Asn Ile Phe Ile Leu Asn Leu Cys Leu Ser Asp Leu Val Phe
65                  70                  75                  80
Ala Cys Leu Leu Pro Val Trp Ile Ser Pro Tyr His Trp Gly Trp Val
                85                  90                  95
```

```
Leu Gly Asp Phe Leu Cys Lys Leu Leu Asn Met Ile Phe Ser Ile Ser
                100                 105                 110

Leu Tyr Ser Ser Ile Phe Phe Leu Thr Ile Met Thr Ile His Arg Tyr
            115                 120                 125

Leu Ser Val Val Ser Pro Leu Ser Thr Leu Arg Val Pro Thr Leu Arg
        130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
        195                 200                 205

Leu Arg Thr Leu Phe Arg Ser Arg Ser Lys Arg Arg His Arg Thr Val
    210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
        275                 280                 285

Phe Val Gly Val Lys Phe Arg Thr His Leu Lys His Val Leu Arg Gln
    290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330

<210> SEQ ID NO 3
<211> LENGTH: 114
<212> TYPE: PRT
<213> ORGANISM: Homo sapiens

<400> SEQUENCE: 3

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 4
```

-continued

```
<211> LENGTH: 165
<212> TYPE: PRT
<213> ORGANISM: Homo sapiens

<400> SEQUENCE: 4

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 5
<211> LENGTH: 165
<212> TYPE: PRT
<213> ORGANISM: Homo sapiens

<400> SEQUENCE: 5

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

```
<210> SEQ ID NO 6
<211> LENGTH: 300
<212> TYPE: PRT
<213> ORGANISM: Artificial Sequence
<220> FEATURE:
<223> OTHER INFORMATION: Synthetic Polypeptide- PAS linker

<400> SEQUENCE: 6

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
                85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro
        115                 120                 125

Ala Ser Pro Ala Ala Pro Ala Pro Ser Ala Pro Ala Ala Ser Pro Ala
    130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala Ala Ser Pro Ala Ala Pro Ala Pro
        195                 200                 205

Ala Ser Pro Ala Ala Pro Ala Pro Ser Ala Pro Ala Ala Ser Pro Ala
    210                 215                 220

Ala Pro Ala Pro Ala Ser Pro Ala Ala Pro Ala Pro Ser Ala Pro Ala
225                 230                 235                 240

Ala Ser Pro Ala Ala Pro Ala Pro Ala Ser Pro Ala Ala Pro Ala Pro
                245                 250                 255

Ser Ala Pro Ala Ala Ser Pro Ala Ala Pro Ala Pro Ala Ser Pro Ala
            260                 265                 270

Ala Pro Ala Pro Ser Ala Pro Ala Ala Ser Pro Ala Ala Pro Ala Pro
        275                 280                 285

Ala Ser Pro Ala Ala Pro Ala Pro Ser Ala Pro Ala
    290                 295                 300
```